(12) United States Patent
Kitamura et al.

(10) Patent No.: US 9,959,618 B2
(45) Date of Patent: May 1, 2018

(54) IMAGE PROCESSING APPARATUS, IMAGE PROCESSING METHOD, AND COMPUTER-READABLE RECORDING MEDIUM

(71) Applicant: OLYMPUS CORPORATION, Tokyo (JP)

(72) Inventors: Makoto Kitamura, Hachioji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 68 days.

(21) Appl. No.: 15/267,544

(22) Filed: Sep. 16, 2016

(65) Prior Publication Data
US 2017/0004620 A1 Jan. 5, 2017

Related U.S. Application Data

(63) Continuation of application No. PCT/JP2015/052870, filed on Feb. 2, 2015.

(30) Foreign Application Priority Data

Mar. 17, 2014 (JP) ................................ 2014-054126

(51) Int. Cl.
*G06K 9/00* (2006.01)
*G06T 7/00* (2017.01)
(Continued)

(52) U.S. Cl.
CPC .......... *G06T 7/0012* (2013.01); *A61B 1/0005* (2013.01); *A61B 1/00009* (2013.01);
(Continued)

(58) Field of Classification Search
CPC ......... G06T 7/0012; G06T 2207/10068; G06T 2207/30092; G06T 2207/10016;
(Continued)

(56) References Cited

U.S. PATENT DOCUMENTS 7,088,850 B2 * 8/2006 Wei ...................... G06T 7/0012
382/128
7,756,309 B2 * 7/2010 Gholap ............. G06F 17/30247
382/128
(Continued)

FOREIGN PATENT DOCUMENTS

CN 102469925 A 5/2012
JP 2006-320650 A 11/2006
(Continued)

OTHER PUBLICATIONS

Japanese Office Action dated Aug. 8, 2017 in Japanese Patent Application No. 2014-054126.
(Continued)

*Primary Examiner* — Li Liu
(74) *Attorney, Agent, or Firm* — Scully, Scott, Murphy & Presser, P.C.

(57) ABSTRACT

An image processing apparatus includes: a detecting unit configured to detect images of interest including regions of interest that are estimated as an object to be detected, from a group of a series of images acquired by sequentially imaging a lumen of a living body; a global similarity calculating unit configured to calculate a global similarity that is a similarity between regions including at least regions other than the regions of interest, between the images of interest different from one another; an image-of-interest group extracting unit configured to extract an image-of-interest group including identical regions of interest, in accordance with comparison between a threshold and the global similarity or a determination parameter based on the global similarity; and a representative image extracting unit configured to extract a representative image from the image-of-interest group.

22 Claims, 20 Drawing Sheets

(51) Int. Cl.
  *A61B 1/00* (2006.01)
  *A61B 1/04* (2006.01)
  *G06T 7/73* (2017.01)
  *G06T 7/90* (2017.01)
  *A61B 5/02* (2006.01)
  *A61B 5/00* (2006.01)

(52) U.S. Cl.
  CPC .......... *A61B 1/041* (2013.01); *A61B 5/02042* (2013.01); *A61B 5/4216* (2013.01); *A61B 5/4255* (2013.01); *G06T 7/0016* (2013.01); *G06T 7/73* (2017.01); *G06T 7/90* (2017.01); *A61B 5/4233* (2013.01); *A61B 5/4238* (2013.01); *A61B 2576/02* (2013.01); *G06T 2207/10016* (2013.01); *G06T 2207/10024* (2013.01); *G06T 2207/10068* (2013.01); *G06T 2207/30101* (2013.01)

(58) Field of Classification Search
  CPC .......... G06T 2207/10024; G06T 7/0016; G06T 7/11; G06T 7/174; G06T 7/32; G06T 7/33; G06K 2209/05; G06K 9/4652
  See application file for complete search history.

(56) References Cited

U.S. PATENT DOCUMENTS

| | | | |
|---|---|---|---|
| 2004/0093166 A1* | 5/2004 | Kil | ............ G01N 1/06 702/19 |
| 2007/0195165 A1 | 8/2007 | Hirakawa | |
| 2008/0119691 A1 | 5/2008 | Yagi et al. | |
| 2009/0309961 A1* | 12/2009 | Miyashita | ............ G06K 9/6251 348/65 |
| 2012/0114203 A1 | 5/2012 | Hirota | |
| 2013/0190600 A1* | 7/2013 | Gupta | .................. A61B 8/0866 600/410 |
| 2014/0376792 A1* | 12/2014 | Matsuzaki | ......... A61B 1/00009 382/128 |
| 2016/0379363 A1* | 12/2016 | Kitamura | .......... G06F 17/30799 600/371 |

FOREIGN PATENT DOCUMENTS

| | | |
|---|---|---|
| JP | 2010-158308 A | 7/2010 |
| JP | 2011-024277 A | 2/2011 |
| JP | 2011-024727 A | 2/2011 |
| JP | 2013-183912 A | 9/2013 |
| WO | WO 2006/100808 A1 | 9/2006 |

OTHER PUBLICATIONS

Chinese Office Action dated Jul. 4, 2017 in Chinese Patent Application No. 201580014177.X.
International Search Report dated Apr. 21, 2015 issued in PCT/JP2015/052870.

\* cited by examiner

IMAGE PROCESSING APPARATUS, IMAGE PROCESSING METHOD, AND COMPUTER-READABLE RECORDING MEDIUM

CROSS REFERENCES TO RELATED APPLICATIONS

This application is a continuation of PCT international application Ser. No. PCT/JP2015/052870, filed on Feb. 2, 2015 which designates the United States, incorporated herein by reference, and which claims the benefit of priority from Japanese Patent Application No. 2014-054126, filed on Mar. 17, 2014, incorporated herein by reference.

BACKGROUND

1. Technical Field

The disclosure relates to an image processing apparatus, an image processing method, and a computer-readable recording medium, for extracting a representative image from an image group acquired by imaging a lumen of a living body.

2. Related Art

A technique has been known in which a group of a series of images (hereinafter, also referred to as intraluminal image group) is obtained by imaging a lumen of a living body in chronological order using a medical observation apparatus such as an endoscope or a capsule endoscope, and an image showing a region of interest such as an abnormal region is extracted as a representative image from the group of a series of images. A user can observe the representative image extracted from the image group, so that a burden during detailed observation of a large number of images is reduced, and diagnosis is made accurately and efficiently.

For example, JP 2011-24727 A discloses an image processing apparatus in which regions of interest are detected from an intraluminal image group obtained in chronological order, the detected regions of interest are classified, based on the features thereof, into identical groups of chronologically adjacent regions of interest having similar features, a representative region of each group is selected from the regions of interest classified in each group, based on an average value of the features, and an image including the selected representative region is output as a representative image.

SUMMARY

In some embodiments, an image processing apparatus includes: a detecting unit configured to detect images of interest including regions of interest that are estimated as an object to be detected, from a group of a series of images acquired by sequentially imaging a lumen of a living body; a global similarity calculating unit configured to calculate a global similarity that is a similarity between regions including at least regions other than the regions of interest, between the images of interest different from one another; an image-of-interest group extracting unit configured to extract an image-of-interest group including identical regions of interest, in accordance with comparison between a threshold and the global similarity or a determination parameter based on the global similarity; and a representative image extracting unit configured to extract a representative image from the image-of-interest group.

In some embodiments, provided is an image processing method for causing a calculation unit of a computer to perform image processing based on image data of a group of a series of images which are acquired by sequentially imaging a lumen of a living body and recorded in a recording unit. The method includes: detecting images of interest including regions of interest, from the group of a series of images; calculating a global similarity that is a similarity between regions including at least regions other than the regions of interest, between the images of interest different from one another; extracting an image-of-interest group including identical regions of interest, in accordance with comparison between a threshold and the global similarity or a determination parameter based on the global similarity; and extracting a representative image from the image-of-interest group.

In some embodiments, provided is a non-transitory computer-readable recording medium with an executable program stored thereon. The program causes a computer to execute: detecting images of interest including regions of interest, from a group of a series of images acquired by sequentially imaging a lumen of a living body; calculating a global similarity that is a similarity between regions including at least regions other than the regions of interest, between the images of interest different from one another; extracting an image-of-interest group including identical regions of interest, in accordance with comparison between a threshold and the global similarity or a determination parameter based on the global similarity; and extracting a representative image from the image-of-interest group.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an image processing apparatus, an image processing method, and an image processing program according to embodiments of the present invention will be described with reference to the drawings. The present invention is not limited to these embodiments. The same reference signs are used to designate the same elements throughout the drawings.

First Embodiment

Figure 1:
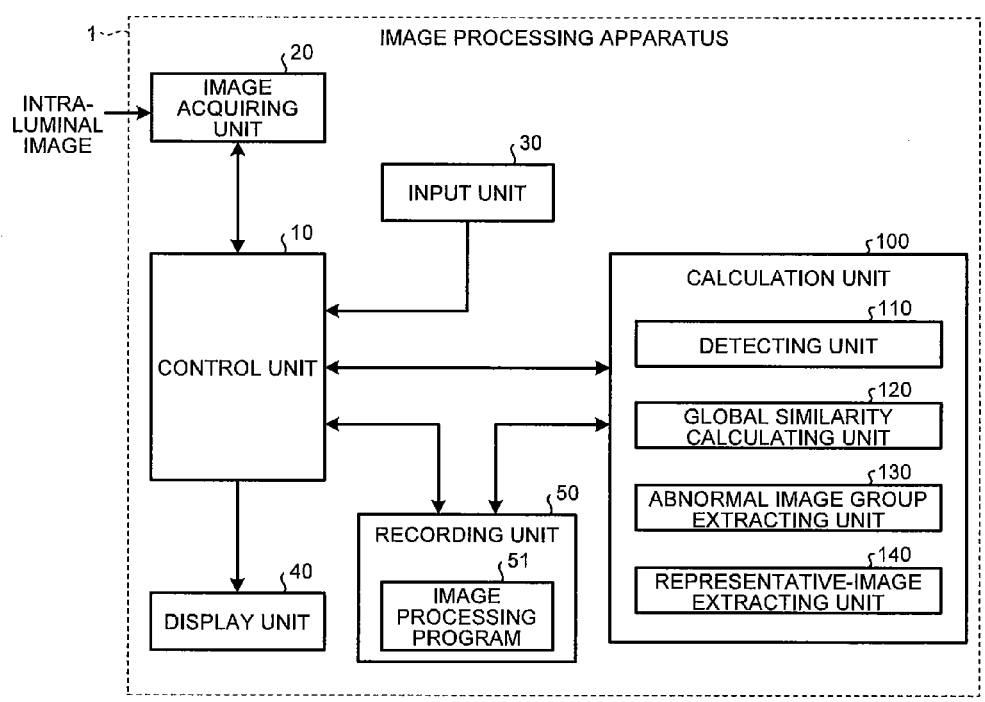
FIG. 1 is a block diagram illustrating a configuration of an image processing apparatus according to a first embodiment of the present invention.

FIG. 1 is a block diagram illustrating an image processing apparatus according to a first embodiment of the present invention. An image processing apparatus 1 according to the first embodiment is an apparatus for extracting an image (image of interest) group including regions of interest that are estimated to be an object to be detected, from a group of a series of images acquired by sequentially imaging a lumen of a living body as a subject by a medical observation apparatus such as a capsule endoscope, and further extracting a representative image from the extracted image-of-interest group. An image showing the lumen of the living body (also referred to as intraluminal image) is normally a color image having a pixel level (pixel value) corresponding to wavelength components of R (red), G (green), and B (blue) at each pixel position. In the following description, abnormal regions such as bleeding, redness, aphtha, and ulcer are detected as the region of interest, and a representative image is extracted from an image-of-interest (abnormal image) group having images including the abnormal regions, but the region of interest is not limited to the above-exemplified abnormal regions.

As illustrated in FIG. 1, the image processing apparatus 1 includes a control unit 10 for controlling the operation of the image processing apparatus 1 as a whole, an image acquiring unit 20 for acquiring image data corresponding to an intraluminal image captured by the medical observation apparatus such as a capsule endoscope, an input unit 30 for inputting a signal to the control unit 10, according to operation from outside, a display unit 40 for displaying various information or images, a recording unit 50 for storing the image data acquired by the image acquiring unit 20 or various programs, and a calculation unit 100 for performing predetermined image processing on the image data.

The control unit 10 includes hardware such as a CPU. The control unit 10 reads the various programs recorded in the recording unit 50 to perform transfer or the like of an instruction or data to each unit of the image processing apparatus 1, according to image data input from the image acquiring unit 20, or a signal or the like input from the input unit 30, and the operation of the image processing apparatus 1 is collectively controlled as a whole.

When a system includes a capsule endoscope for imaging the inside of the subject, the image acquiring unit 20 is appropriately configured depending on a mode of the system. For example, when a portable recording medium is used to transmit and receive image data to and from the capsule endoscope, the image acquiring unit 20 includes a reader device removably mounting the recording medium to read image data of recorded images. In addition, when a server is provided to save image data of images captured by the capsule endoscope, the image acquiring unit 20 includes a communication device or the like connected to the server, and performs data communication with the server to acquire the image data.

The input unit 30 includes for example an input device such as a keyboard, a mouse, a touch panel, or various switches, and outputs, to the control unit 10, an input signal generated according to the operation from outside to the input device.

The display unit 40 includes a display device such as an LCD or an EL display, and displays various screens including the intraluminal image under control of the control unit 10.

The recording unit 50 includes various IC memories including a RAM, and a ROM such as a flash memory for updatable recording, a hard disk incorporated or connected with a data communication terminal, or an information recording device such as a CD-ROM and a reader or the like therefor. The recording unit 50 stores the programs for operating the image processing apparatus 1 and causing the image processing apparatus 1 to perform various functions, data used during execution of the programs, or the like, in addition to the image data of the intraluminal image acquired by the image acquiring unit 20. Specifically, the recording unit 50 stores an image processing program 51, determination criteria used to detect abnormal regions, determination criteria used to extract a representative image, and the like. The image processing program 51 causes the image processing apparatus 1 to perform image processing for detecting the abnormal regions such as bleeding, redness, aphtha, ulcer, and the like from the intraluminal images, extracting abnormal image groups each including identical abnormal regions from images (abnormal images) including these abnormal regions, and extracting a representative image from each of the abnormal image groups.

The calculation unit 100 includes hardware such as a CPU, reads the image processing program 51 to perform image processing for extracting abnormal image groups each including identical abnormal regions, from the intraluminal images, and extracting a representative image from each abnormal image group.

Next, a configuration of the calculation unit 100 will be described. As illustrated in FIG. 1, the calculation unit 100 includes a detecting unit 110 for detecting abnormal images including abnormal regions from a group of a series of intraluminal images, a global similarity calculating unit 120 for calculating a global similarity being an overall similarity between different abnormal images, an abnormal image group extracting unit 130 for extracting abnormal image groups each including identical abnormal regions from the abnormal images detected by the detecting unit 110, based on the global similarity, and a representative-image extracting unit 140 for extracting a representative image from each of the extracted abnormal image groups.

The detecting unit 110 detects abnormal regions based on various features of the intraluminal images. In the first embodiment, description will be made of an example of detecting the abnormal region based on color features (color information) of the intraluminal image. Here, an abnormal region such as bleeding, redness, or vascular abnormality is indicated by a specific reddish color, and an abnormal region such as ulcer or aphtha is indicated by a specific whitish color. The detecting unit 110 uses color features, for example, color components (R component, G component, B component) of the pixel value, or values secondarily calculated by a known conversion from the color components (e.g., color difference calculated by YCbCr conversion, hue and saturation calculated by HSI conversion, color ratio such as G/R or B/G) to detect a region indicated by any of the specific colors in the intraluminal image, and defines the region as the abnormal region. The detecting unit 110, more specifically, previously develops determination criteria (color range) for abnormal regions, based on color features of various abnormal regions having been collected, and records the determination criteria in the recording unit 50. When an abnormal region is detected from the intraluminal image, the determination criteria are read from the recording unit 50, color features are calculated for each pixel constituting the intraluminal image, the color features of each pixel are compared with the determination criteria, and the abnormal region is detected from the intraluminal image.

Note that detection of an abnormal region is not limited to the above-mentioned method, and various known methods can be applied as long as the abnormal region can be detected. For example, a method based on a feature space distance with a representative color feature may be used. Further, in the above description, the color features of a pixel constituting the intraluminal image is used to detect the abnormal region, but the intraluminal image may be divided into small regions based on edge information or the like in the image so that color features of a small region is used to detect the abnormal region. Still further, the abnormal region may be detected using shape features or texture features other than the color features.

The global similarity calculating unit 120 calculates, as the global similarity, a similarity between at least regions including regions other than the abnormal regions, that is, regions including backgrounds of the abnormal regions, between different abnormal images.

The abnormal image group extracting unit 130 is an image-of-interest group extracting unit for extracting, as one abnormal image group, images including identical abnormal regions from the abnormal regions detected by the detecting unit 110, based on the global similarity calculated by the global similarity calculating unit 120.

The representative-image extracting unit 140 extracts a representative image from each abnormal image group including identical abnormal regions. A method for extracting a representative image is not particularly limited. The first or middle time-series image of an abnormal image group may be merely extracted as the representative image, or an abnormal image including an abnormal region having a high degree of importance for image diagnosis or an abnormal image having good visibility of an abnormal region may be extracted as the representative image. The degree of importance or visibility of the abnormal region can be determined based on for example color features, shape features, texture features, or the like of the abnormal region.

Figure 2:
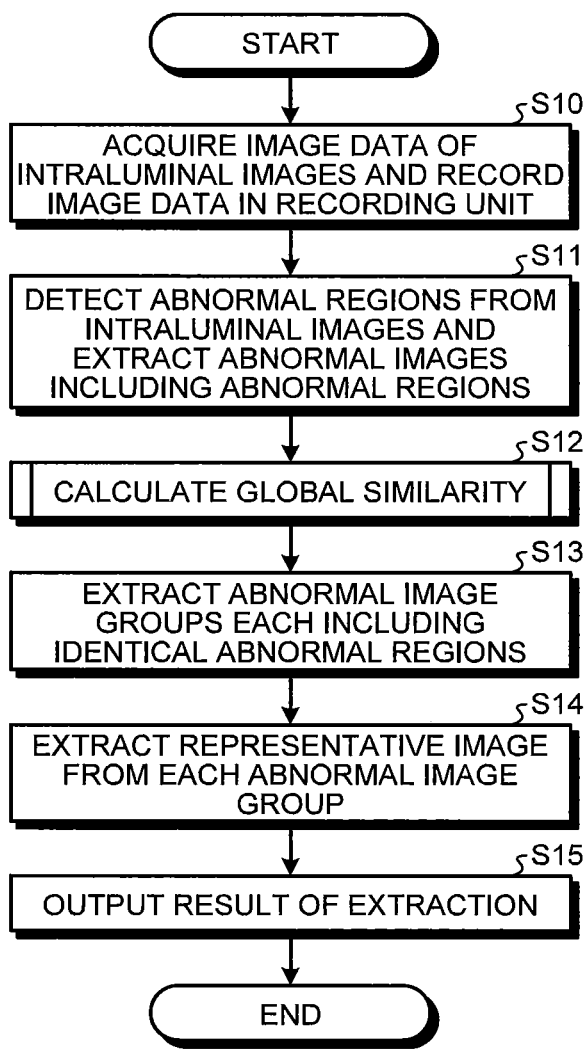
FIG. 2 is a flowchart illustrating operation of the image processing apparatus illustrated in FIG. 1.

Next, operation of the image processing apparatus 1 illustrated in FIG. 1 will be described. FIG. 2 is a flowchart illustrating the operation of the image processing apparatus 1. First, in step S10, the image processing apparatus 1 acquires image data of a series of intraluminal images captured in chronological order through the image acquiring unit 20, and records the image data in the recording unit 50.

In the following step S11, the detecting unit 110 sequentially reads the image data of the intraluminal images recorded in the recording unit 50, detects abnormal regions from the intraluminal images, and extracts abnormal images including the abnormal regions. Specifically, the detecting unit 110 reads the determination criteria for abnormal regions previously recorded in the recording unit 50, compares each of the color features of the pixels constituting the intraluminal images, with this determination criteria, and detects the abnormal regions.

Figure 3:
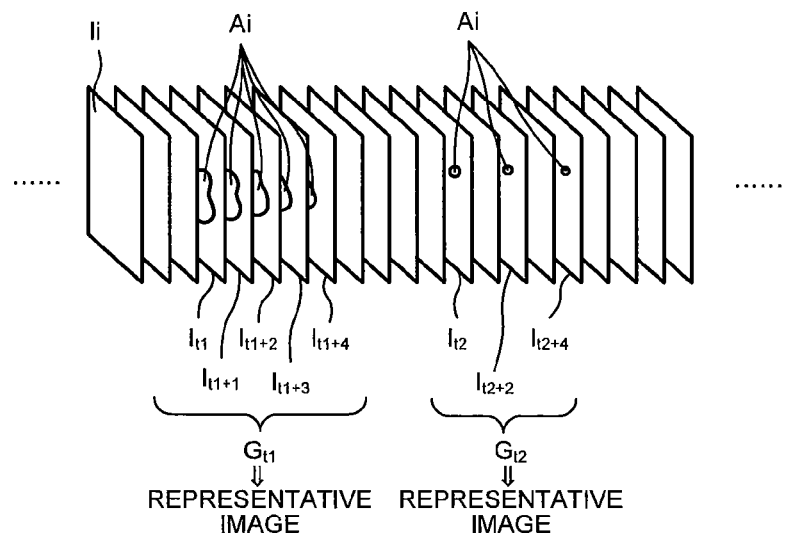
FIG. 3 is a schematic diagram illustrating a series of intraluminal images acquired in chronological order.

FIG. 3 is a schematic diagram illustrating the series of intraluminal images $I_i$ acquired in chronological order. Here, a subscript i (i=1, 2, . . . ) represents an time-series arrangement order (capturing order) of the intraluminal images, and corresponds to an image number. In the process of step S11, abnormal regions $A_i$ (i=t1 to t1+4, t2, t2+2, t2+4) are detected, and the intraluminal images $I_i$ including the abnormal regions $A_i$ are extracted. Hereinafter, the intraluminal images $I_i$ including the abnormal regions $A_i$ are referred to as abnormal images $I_i$, and an image sequence consisting only of the abnormal images $I_i$ arranged in chronological order (capturing order) is referred to as an abnormal image sequence.

In the following step S12, the global similarity calculating unit 120 calculates a global similarity between adjacent abnormal images in the abnormal image sequence, for the abnormal images extracted in step S11. For example, in FIG. 3, the global similarities are calculated for combinations of abnormal images $I_{t1}$ and $I_{t1+1}$, abnormal images $I_{t1+1}$ and $I_{t1+2}$, abnormal images $I_{t1+2}$ and $I_{t1+3}$, abnormal images $I_{t1+3}$ and $I_{t1+4}$, abnormal images $I_{t1+4}$ and $I_{t2}$, abnormal images $I_{t2}$ and $I_{t2+2}$, and abnormal images $I_{t2+2}$ and $I_{t2+4}$ as the adjacent abnormal images in the abnormal image sequence.

Figure 4:
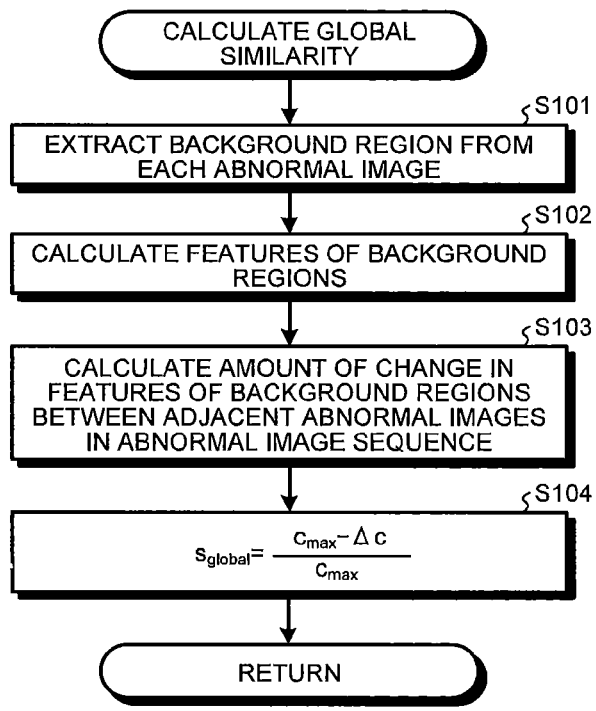
FIG. 4 is a flowchart illustrating a global similarity calculation process performed by a global similarity calculating unit illustrated in FIG. 1.

In the first embodiment, an example of calculation of a similarity, as the global similarity, between background regions of abnormal regions will be described. FIG. 4 is a flowchart illustrating a global similarity calculation process performed by the global similarity calculating unit 120 in step S12. Furthermore, FIG. 5 is a schematic diagram illustrating the global similarity calculation process.

Figure 5:
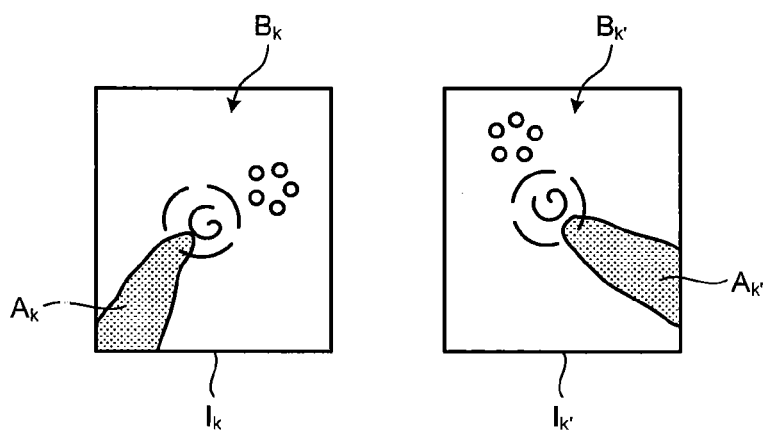
FIG. 5 is a schematic diagram illustrating the global similarity calculation process performed by the global similarity calculating unit illustrated in FIG. 1.

As illustrated in FIG. 5, abnormal regions $A_k$ and $A_{k'}$ are detected respectively from adjacent abnormal images $I_k$ and $I_{k'}$ (k and k' are a natural number, where k<k') in an abnormal image sequence. In this condition, in step S101 illustrated in FIG. 4, the global similarity calculating unit 120 extracts, as the background region, regions other than the abnormal regions $A_k$ and $A_{k'}$, that is, non-abnormal regions $B_k$ and $B_{k'}$, from the abnormal images $I_k$ and $I_{k'}$.

In the following step S102, the global similarity calculating unit 120 calculates features $c_k$ and $c_{k'}$ of the background regions, that is, the non-abnormal regions $B_k$ and $B_{k'}$. The features $c_k$ and $c_{k'}$ include for example a statistic such as an average value, median, or the like of pixel values (luminance values or G component values) of pixels constituting the non-abnormal regions $B_k$ and $B_{k'}$, a statistic such as an average value, median, or the like of color features (color difference calculated by YCbCr conversion, a hue or saturation calculated by HSI conversion, a color ratio such as G/R or B/G, or the like, using R component, G component, and B component values) of pixels constituting the non-abnormal regions $B_k$ and $B_{k'}$, and a statistic such as an average value, median, or the like of shape features (areas, circularity, or the like) of the non-abnormal regions $B_k$ and $B_{k'}$, or texture features (edge amounts or the like calculated using Sobel filter, Laplacian filter, or the like) in pixels constituting the non-abnormal regions $B_k$ and $B_{k'}$.

In the following step S103, the global similarity calculating unit 120 calculates an amount of change $\Delta c$ ($\Delta c = c_k - c_{k'}$) in features $c_k$ and $c_{k'}$ of the non-abnormal regions $B_k$ and $B_{k'}$ between the adjacent abnormal images $I_k$ and $I_{k'}$ in the abnormal image sequence.

In the following step S104, the global similarity calculating unit 120 calculates a global similarity $s_{global}$ given by the following formula (1) using a maximum value $c_{max}$ and the amount of change $\Delta c$ in features.

$$s_{global} = (c_{max} - \Delta c)/c_{ma} \quad (1)$$

In formula (1), the maximum value $c_{max}$ of the features is a maximum value that the features $c_k$ and $c_{k'}$ may take. For example, if statistical values of pixel values (G component values) are calculated as the features $c_k$ and $c_{k'}$ for the abnormal images $I_k$ and $I_{k'}$ having 256 tones, the maximum value $c_{max}$ is 256. If circularity is calculated as the features $c_k$ and $c_{k'}$, the maximum value $c_{max}$ is 1. Then, the operation of the image processing apparatus 1 returns to a main routine.

In step S13 subsequent to step S12, the abnormal image group extracting unit 130 extracts abnormal image groups each including identical abnormal regions, from the abnormal images extracted in step S11, based on the calculated global similarity $s_{global}$ calculated in step S12. Particularly, the abnormal image group extracting unit 130 determines abnormal images having a global similarity $s_{global}$ not less than a predetermined threshold, as abnormal images including identical abnormal regions. In contrast, the abnormal image group extracting unit 130 determines abnormal images having a global similarity $s_{global}$ less than the predetermined threshold, as abnormal images not including identical abnormal regions. Then, the abnormal image group extracting unit 130 extracts the abnormal images including identical abnormal regions, as one abnormal image group.

For example, in FIG. 3, when the abnormal images $I_{t1}$ and $I_{t1+1}$, the abnormal images $I_{t1+1}$ and $I_{t1+2}$, the abnormal images $I_{t1+2}$ and $I_{t1+3}$, and the abnormal images $I_{t1+3}$ and $I_{t1+4}$ are determined to include the identical abnormal regions, respectively, these abnormal images $I_{t1}$, $I_{t1+1}$, $I_{t1+2}$, $I_{t1+3}$, and $I_{t1+4}$ are extracted as one abnormal image group $G_{t1}$. Further, when the abnormal images $I_{t1+4}$ and $I_{t2}$ are determined not to include identical abnormal regions, the abnormal image $I_{t2}$ is not extracted as the abnormal image group in which the abnormal image $I_{t1+4}$ is included. Still further, when the abnormal images $I_{t2}$ and $I_{t2+2}$, and the abnormal images $I_{t2+2}$ and $I_{t2+4}$ are determined to include identical abnormal regions, respectively, these abnormal images $I_{t2}$, $I_{t2+2}$, and $I_{t2+4}$ are extracted as one abnormal image group $G_{t2}$.

In the following step S14, the representative-image extracting unit 140 extracts a representative image from each of the abnormal image groups extracted in step S13. The number of representative images to be extracted may have a constant value (e.g., one from each abnormal image group), or may be determined according to the number of abnormal images included in an abnormal image group (e.g., a times the number of abnormal images, where $0<\alpha<1$). Note that, when the number of representative images is determined according to the number of abnormal images, even if the number of representative images is less than one, at least one representative image is extracted. Alternatively, all abnormal images satisfying a predetermined criterion (e.g., abnormal images having a color feature not less than a predetermined threshold) may be extracted as the representative image, without specifying the number of representative images to be extracted.

A method for extracting a representative image is not particularly limited. For example, the first or middle time-series image of each abnormal image group may be extracted as the representative image. Alternatively, the representative image may be extracted based on the color features of identical abnormal regions in each abnormal image group. Specifically, when an abnormal region is indicated by the specific reddish color, an abnormal image having a stronger red color in the abnormal region is preferentially extracted as the representative image, and when an abnormal region is indicated by the specific whitish color, an abnormal image having a stronger white color in the abnormal region is preferentially extracted as the representative image. Furthermore, an abnormal image having an abnormal region larger in size, or an abnormal image having an abnormal region positioned near the center may be preferentially extracted as the representative image.

In the following step S15, the calculation unit 100 outputs, as a result of extraction of the representative image, information indicating the representative image extracted from each of the abnormal image groups in step S14. Accordingly, the recording unit 50 adds information (flag) indicating the representative image to image data of an intraluminal image extracted as the representative image.

As described above, according to the first embodiment of the present invention, since an abnormal image group is extracted based on the global similarity between regions including the background regions, in abnormal images, the abnormal images can be extracted as the identical abnormal image group, even if the abnormal region significantly changes in position, shape, or color between the abnormal images, or the abnormal region is out of view for a moment and the abnormal images are temporally separated from each other, depending on conditions of imaging the abnormal region. Therefore, abnormal images showing identical abnormal regions can be prevented from being continuously extracted as the representative images. Accordingly, observing extracted representative images restricted in number but covering all detected abnormal regions allows the user to make accurate and efficient diagnosis.

Modification 1-1

Next, modification 1-1 of the first embodiment of the present invention will be described.

The background region extracted from each abnormal image for calculating the global similarity may not be whole of the non-abnormal region. For example, regions (mucosal regions) showing a mucosa may be extracted from abnormal images, as the background regions, to calculate a global similarity between the mucosal regions.

The mucosal region can be extracted using determination criteria previously developed. The determination criteria are developed by a learning tool such as a support vector machine (SVM), based on a feature distribution of a non-mucosal region such as bleeding, residue, bubbles, halation, or a dark portion shown in an intraluminal image, and stored in the recording unit 50. The feature includes color features (values of R component, G component, and B component of a pixel value, values secondarily calculated by known conversion based on the values of these color components (color difference calculated by YCbCr conversion, hue or saturation calculated by HSI conversion, color ratio such as G/R or B/G, or the like)), shape features (shape information such as histograms of oriented gradients (HOG), area, circumferential length, or Feret's diameter), and texture features (local binary pattern (LBP), simultaneous normal matrix, or the like).

Figure 6:
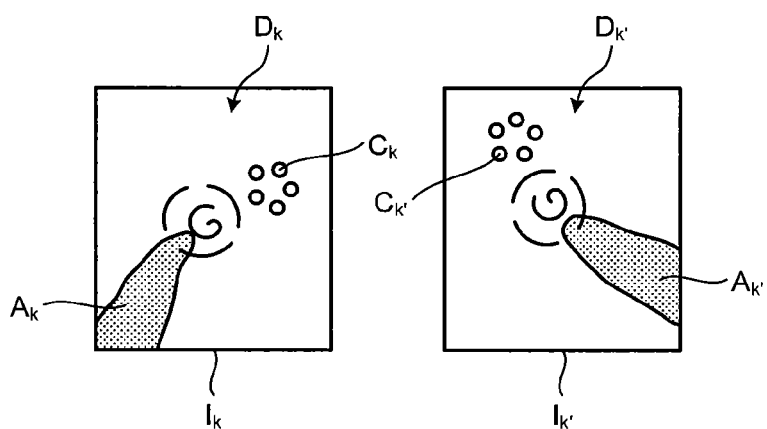
FIG. 6 is a schematic diagram illustrating a global similarity calculation process according to modification 1-1 of the first embodiment of the present invention.

FIG. 6 is a schematic diagram illustrating a global similarity calculation process (see step S12 of FIG. 2, and FIG. 4) according to modification 1-1. In this configuration, in step S101, the global similarity calculating unit 120 reads determination criteria for determining a mucosal region, from the recording unit 50, compares features calculated for pixels constituting an abnormal image with the determination criteria, and extracts a mucosal region. Therefore, as illustrated in FIG. 6, mucosal regions $D_k$ and $D_{k'}$ are extracted from adjacent abnormal images $I_k$ and $I_{k'}$ in the abnormal image sequence. From the mucosal regions $D_k$, and $D_{k'}$, abnormal regions $A_k$ and $A_{k'}$ such as bleeding or unnecessary regions $C_k$ or $C_{k'}$ such as bubbles are excluded.

The global similarity calculating unit 120 calculates the features $c_k$ and $c_{k'}$ with the mucosal regions $D_k$ and $D_{k'}$ as the background region (see step S102), and uses the maximum value $c_{max}$ and the amount of change $\Delta c$ in features to calculate the global similarity $s_{global}$ given by formula (1) (see steps S103 and S104).

As described above, according to modification 1-1, since the global similarity between mucosal regions is calculated between abnormal images, the abnormal image group including identical abnormal regions can be extracted, while inhibiting influence caused by a local phenomenon, such as bleeding, residue, bubbles, halation, or a dark portion.

Modification 1-2

Next, modification 1-2 of the first embodiment of the present invention will be described.

The global similarity may be calculated based on a feature of a region including an abnormal region, in addition to the background region. Specifically, the global similarity may be calculated based on a feature of the whole abnormal image including the abnormal region and the non-abnormal region. Alternatively, a feature of a region obtained by excluding an unnecessary region (region other than an object to be detected in diagnosis), such as residue, bubbles, halation, or a dark portion, from the whole abnormal image may be used to calculate the global similarity. In any case, the global similarity is preferably employed as long as the global similarity is calculated between regions each including at least a non-abnormal region.

Modification 1-3

Next, modification 1-3 of the first embodiment of the present invention will be described.

The global similarity between abnormal images may be determined based on types of organ shown in the abnormal images. Hereinafter, a method of determining the global similarity based on the types of organ will be described.

First, the types of organ shown in each abnormal image is determined. The types of organ can be determined using various known methods. A method disclosed in JP 2006-288612 A will be described below as an example. First, a numerical range of each of color components (color elements) R, G, and B in an image showing each organ (esophagus, stomach, small intestine, or large intestine) in a lumen is previously determined. Then, respective average values of R components, G components, and B components of pixels constituting an abnormal image are calculated, and the average values are compared with the previously determined numerical ranges of the color components of the organs. Thus, when the average values of the color components calculated for the abnormal image are within the previously determined numerical ranges of the color components of the esophagus, an organ shown in the abnormal image is determined as esophagus. Similarly, when average values of the color components calculated for the abnormal image are within the previously determined numerical ranges of the color components of the stomach, an organ shown in the abnormal image is determined as stomach, when within the numerical ranges of the color components of the small intestine, an organ shown in the abnormal image is determined as small intestine, and when within the numerical ranges of the color components of the large intestine, an organ shown in the abnormal image is determined as large intestine.

The global similarity calculating unit 120 determines the global similarity based on the types of organ determined for each abnormal image. Specifically, when organs are identical in kind between adjacent abnormal images in an abnormal image sequence, the similarity is determined to be 1.0. In contrast, when organs are different in kind between adjacent abnormal images in an abnormal image sequence, the similarity is determined to be 0.0.

Note that, the types of organ may be determined by the user. Specifically, through image processing in the calculation unit 100, average colors of the series of intraluminal images are calculated, and a color bar in which the average colors are arranged in arrangement order of intraluminal images (time-series order) is formed to be displayed on the display unit 40. A color difference (boundary) between average colors on this color bar corresponds to a boundary between organs in the series of intraluminal images. When a signal for selecting a specific point on the color bar is input from the input unit 30 to the control unit 10, according to the user's operation to the input unit 30, the control unit 10 inputs, to the calculation unit 100, an image number of an intraluminal image corresponding to the selected point. The calculation unit 100 identifies the types of organ shown in each intraluminal image, with an intraluminal image corresponding to the input image number as a boundary of organ. The global similarity calculating unit 120 determines the global similarity, based on the types of organ in intraluminal images from which abnormal regions are detected.

Modification 1-4

Next, modification 1-4 of the second embodiment of the present invention will be described.

After acquisition of the image data in step S10, the calculation unit 100 may perform a process of determining the types of organ for the whole of the series of intraluminal images. Note that, a method for determining the types of organ is similar to that described in modification 1-3, and the types of organ may be automatically determined or manually determined by the user.

In this configuration, the calculation unit 100 performs processing of steps S11 to S14 as described above (see FIG. 2) on intraluminal images showing an organ to be examined (e.g., small intestine). In contrast, the calculation unit 100 detects an abnormal region to extract an abnormal image from intraluminal images showing an organ other than the object to be examined (e.g., esophagus, stomach, large intestine), subsequently extracts a predetermined number (e.g., small number such as ten) of abnormal images, for example, in descending order of intensity in reddish color of the abnormal region, or in descending order of intensity in white color of the abnormal region, and then outputs the abnormal images as the representative images. Note that, the intensity of reddish color is indicated by the color ratio G/R, and the smaller the color ratio G/R, the stronger the reddish color. Furthermore, the intensity of white color is indicated by the color ratios G/R and B/G, and the larger the color ratios G/R and B/G, the stronger the whitish color. Alternatively, the calculation unit 100 may extract a predetermined number (e.g., small number such as ten) of intraluminal images as the representative images, based on the color features (color ratio or the like described above) of the intraluminal images without detecting an abnormal region for the intraluminal images showing an organ other than the object to be examined. Furthermore, the calculation unit 100 does not need to extract the representative image from the intraluminal images showing an organ other than the object to be examined.

Second Embodiment

Next, a second embodiment of the present invention will be described.

Figure 7:
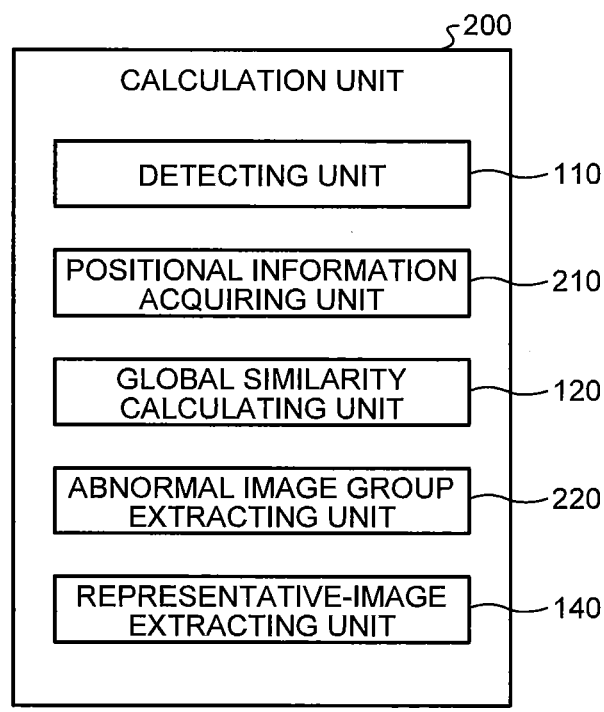
FIG. 7 is a block diagram illustrating a configuration of a calculation unit of an image processing apparatus according to a second embodiment of the present invention.

FIG. 7 is a block diagram illustrating a configuration of a calculation unit of an image processing apparatus according to a second embodiment of the present invention. The image processing apparatus according to the second embodiment includes a calculation unit 200 illustrated in FIG. 7, instead of the calculation unit 100 illustrated in FIG. 1. Configurations and operations of units other than the calculation unit 200 are similar to those of the first embodiment.

The calculation unit 200 includes the detecting unit 110, a positional information acquiring unit 210, the global similarity calculating unit 120, an abnormal image group extracting unit 220, and the representative-image extracting unit 140. Among these, operations of the detecting unit 110, the global similarity calculating unit 120, and the representative-image extracting unit 140 are similar to those of the first embodiment.

The positional information acquiring unit 210 acquires chronological arrangement order (capturing order) or image numbers representing the arrangement order of the abnormal images $I_i$, in the series of intraluminal images (see FIG. 3), or imaging time of each abnormal image $I_i$, as time-series positional information of the abnormal images $I_i$. Here, when a capsule endoscope used for imaging the series of intraluminal images has an average travel speed of v (e.g., 1 mm/second), and an imaging frame rate of F (e.g., 2 frames/second), the imaging position in an intraluminal image (abnormal image) $I_i$ can be estimated to be at a distance i·v/F (mm) from an imaging start position (e.g., in oral cavity) of the series of intraluminal images. Furthermore, similarly, the position of the capsule endoscope can be also estimated using the imaging time. Accordingly, the arrangement order, image number, and imaging time of the intraluminal image can be handled as the positional information of the abnormal image $I_i$.

The abnormal image group extracting unit 220 extracts abnormal image groups each including identical abnormal regions, based on the positional information acquired by the positional information acquiring unit 210, and the global similarity calculated by the global similarity calculating unit 120.

Figure 8:
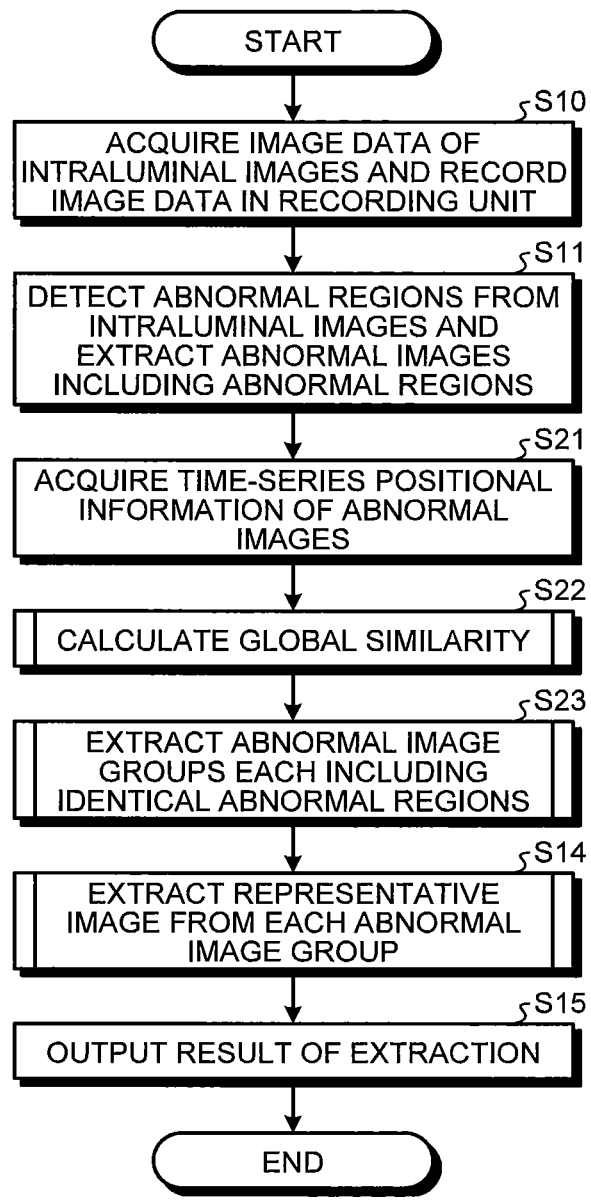
FIG. 8 is a flowchart illustrating operation of the image processing apparatus according to the second embodiment of the present invention.

Next, operation of the image processing apparatus according to the second embodiment will be described. FIG. 8 is a flowchart illustrating operation of the image processing apparatus according to the second embodiment. Note that, steps S10 and S11 illustrated in FIG. 8 are similar to those of the first embodiment (see FIG. 2).

In step S21 subsequent to step S11, the positional information acquiring unit 210 acquires time-series positional information of the abnormal images extracted in step S11. Specifically, the imaging time or the arrangement order i of the abnormal image $I_i$ is acquired as the positional information.

In the following step S22, the global similarity calculating unit 120 calculates the global similarity between adjacent abnormal images in an abnormal image sequence. A method for calculating the global similarity is similar to that described in the first embodiment (see FIGS. 4 and 5). Alternatively, the global similarity may be calculated in a similar manner to modifications 1-1 to 1-3.

In the following step S23, the abnormal image group extracting unit 220 extracts abnormal image groups each including identical abnormal regions, based on the positional information acquired in step S21 and the global similarity calculated in step S22.

Figure 9:
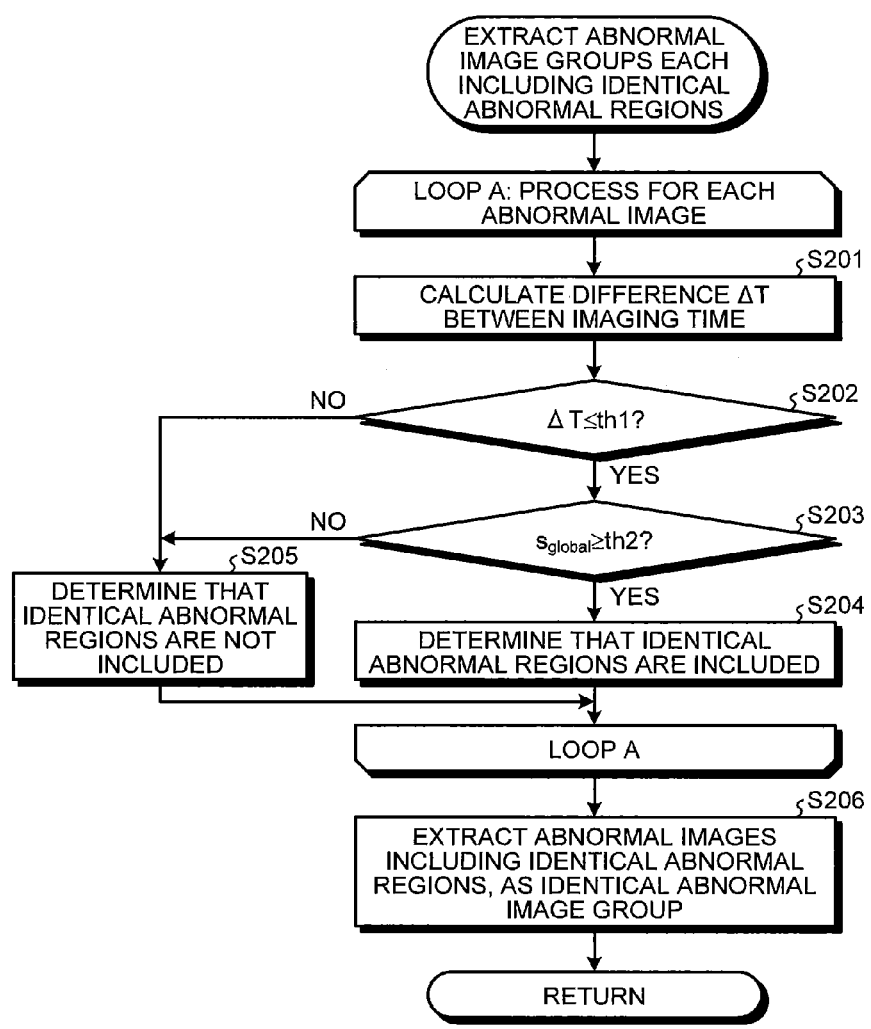
FIG. 9 is a flowchart illustrating an abnormal image group extraction process performed by an abnormal image group extracting unit illustrated in FIG. 7.
Figure 10:
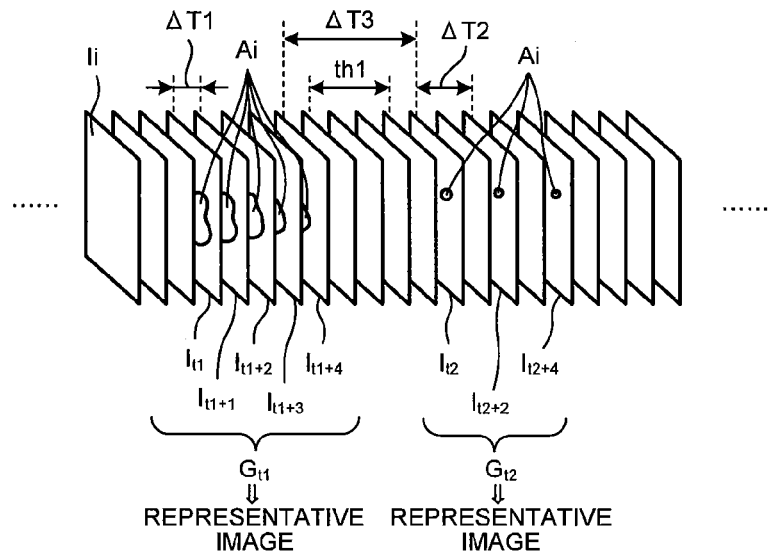
FIG. 10 is a schematic diagram illustrating the abnormal image group extraction process performed by the abnormal image group extracting unit illustrated in FIG. 7.

FIG. 9 is a flowchart illustrating an abnormal image group extraction process performed by the abnormal image group extracting unit 220 in step S23. FIG. 10 is a schematic diagram illustrating the abnormal image group extraction process. The abnormal image group extracting unit 220 performs processing of a loop A for each abnormal image extracted in step S11.

First, in step S201, the abnormal image group extracting unit 220 calculates a difference $\Delta T$ ($=T(I_{k'})-T(I_k)$) between imaging time $T(I_k)$ and $T(I_{k'})$, that is, an elapsed time, between an abnormal image $I_k$ to be processed (k is a natural number) and an adjacent abnormal image $I_{k'}$ (k' is a natural number, where k<k') in an abnormal image sequence.

In the following step S202, the abnormal image group extracting unit 220 determines whether the difference $\Delta T$ between imaging time calculated in step S201 is not more than a predetermined threshold th1.

When the difference $\Delta T$ between imaging time is not more than the threshold th1 (step S202: Yes), the abnormal image group extracting unit 220 then determines whether the global similarity $s_{global}$ between the abnormal images $I_k$ and $I_{k'}$ is not less than a predetermined threshold th2 (step S203).

When the global similarity $s_{global}$ is not less than the threshold th2 (step S203: Yes), the abnormal image group extracting unit 220 determines that the abnormal image $I_k$ to be processed and the abnormal image $I_{k'}$ extracted subsequent to the abnormal image $I_k$ include identical abnormal regions (step S204).

For example, as illustrated in FIG. 10, when an abnormal image $I_{t1}$ and an abnormal image $I_{t1+1}$ adjacent to each other in chronological order ($\Delta T1<th1$) have a global similarity $s_{global}$ not less than the threshold th2, these abnormal images $I_{t1}$ and $I_{t1+1}$ are determined to include identical abnormal regions. Furthermore, when an abnormal image $I_{t2}$ and an abnormal image $I_{t2+2}$, which are not adjacent in chronological order in an intraluminal image group $I_i$ (i=1, 2, . . . ), have a difference $\Delta T2$ between imaging time not more than the threshold th1, the abnormal image $I_{t2}$ and the abnormal image $I_{t2+2}$ are determined to include identical abnormal regions, on condition that the global similarity $s_{global}$ is not less than the threshold th2.

In contrast, when the difference $\Delta T$ between imaging time is larger than the threshold th1 in step S202 (step S202: No), or when the global similarity $s_{global}$ is less than the threshold th2 in step S203 (step S203: No), the abnormal image group extracting unit 220 determines that the abnormal image $I_k$ to be processed and the abnormal image $I_{k'}$ extracted subsequent to the abnormal image $I_k$ do not include identical abnormal regions (step S205). For example, as illustrated in FIG. 10, a difference $\Delta T3$ between imaging time between an abnormal image $I_{t1+4}$ and the abnormal image $I_{t2}$ is larger than the threshold th1, so that these abnormal images are determined not to include identical abnormal regions.

After completion of the processing of the loop A for all abnormal images, the abnormal image group extracting unit 220 extracts abnormal images determined to show identical abnormal regions, as the identical abnormal image group, in step S206. Then, operation of the image processing apparatus returns to a main routine.

Note that, in step S201, a difference in arrangement order i between the abnormal images $I_i$ may be calculated, instead of imaging time. In this condition, in step S202, it is determined whether a difference in arrangement order is not more than a predetermined threshold.

Note that, steps S14 and S15 subsequent to step S22 are similar to those of the first embodiment (see FIG. 2).

As described above, according to the second embodiment of the present invention, since the abnormal image group including identical abnormal regions is extracted based on time-series positional information and the global similarity of the abnormal images, it is possible to prevent abnormal images, which are temporally separated significantly, from being extracted as the identical abnormal image group.

Modification 2

Next, modification 2 of the second embodiment of the present invention will be described.

In the second embodiment, the time-series positional information of the abnormal images is used for the extraction process for the abnormal image group including identical abnormal regions. However, this positional information can be used to perform a representative image extraction process.

Figure 11:
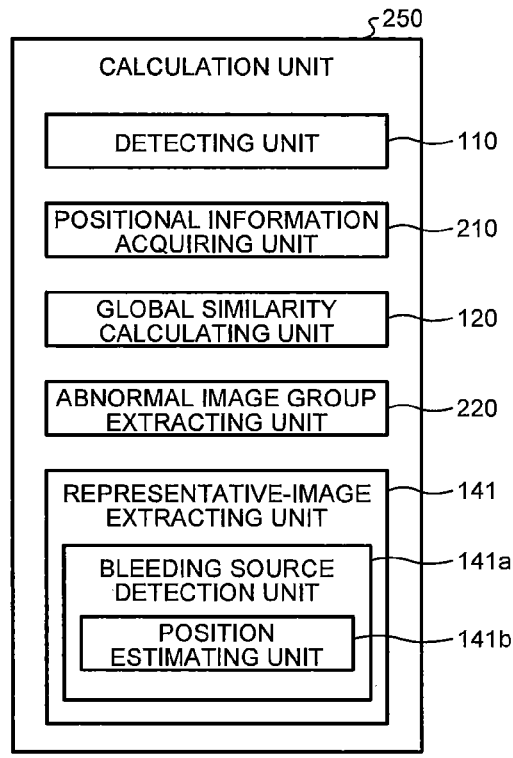
FIG. 11 is a block diagram illustrating a configuration of a calculation unit of an image processing apparatus according to modification 2 of the second embodiment of the present invention.

FIG. 11 is a block diagram illustrating a configuration of a calculation unit of an image processing apparatus according to modification 2. As illustrated in FIG. 11, a calculation unit 250 according to modification 2 includes a representative-image extracting unit 141, instead of the representative-image extracting unit 140 of the calculation unit 200 according to the second embodiment (see FIG. 7). Configurations and operations of units of the calculation unit 250 other than the representative-image extracting unit 141 are similar to those of the second embodiment.

The representative-image extracting unit 141 preferentially extracts, as the representative image, an abnormal image showing a bleeding source for the abnormal region having a high degree of importance, from each of the abnormal image groups each including identical abnormal regions. More specifically, the representative-image extracting unit 141 includes a bleeding source detection unit 141a for detecting a bleeding source from an abnormal image group showing a bleeding abnormal region. The bleeding source detection unit 141a includes a position estimating unit 141b for estimating a position, in a lumen, of a subject (organ) shown in an abnormal image, that is, an imaging position in a lumen from which the abnormal image is captured.

Figure 12:
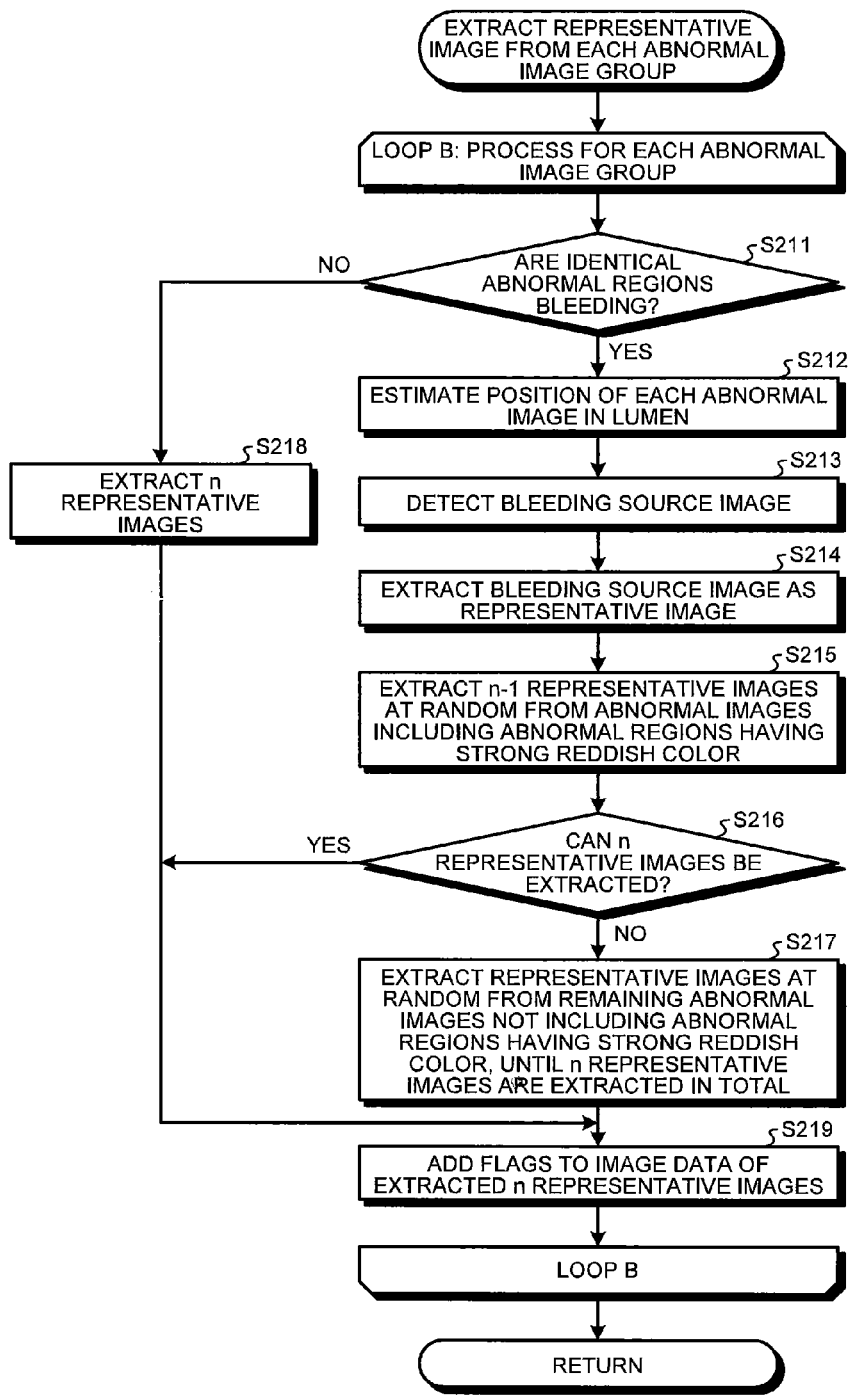
FIG. 12 is a flowchart illustrating a representative-image extraction process performed by a representative-image extracting unit illustrated in FIG. 11.

FIG. 12 is a flowchart illustrating a representative-image extraction process performed by the representative-image extracting unit 141 in step S14 illustrated in FIG. 8. The representative-image extracting unit 141 performs processing of a loop B for each abnormal image group extracted in step S23. Note that, in the following description, the number of representative images to be extracted from each abnormal image group is defined as n.

First, in step S211, the representative-image extracting unit 141 determines whether identical abnormal regions included in an abnormal image group to be processed have bleeding. Specifically, abnormal regions detected based on the specific reddish color in step S11 (see first embodiment) are determined as bleeding. Alternatively, it may be determined whether the abnormal regions have bleeding, based on the color features, the shape features, and the texture features of the abnormal region.

When the identical abnormal regions represent bleeding (step S211: Yes), the position estimating unit 141b captures the time-series positional information (imaging time or arrangement order of abnormal images) acquired by the positional information acquiring unit 210 in step S21, and estimates an imaging position, in a lumen, of each abnormal image included in the abnormal image group, based on the positional information (step S212).

In the following step S213, the bleeding source detection unit 141a detects bleeding source images (abnormal image showing a bleeding source). Specifically, an abnormal image captured at an imaging position on the most upstream side in a lumen (i.e., the oldest time-series abnormal image) is detected, as the bleeding source image, from abnormal images including an abnormal region having a strong reddish color of the abnormal image group. Here, the abnormal region having a strong reddish color can be determined, for example, as a region having a color ratio G/R not more than a predetermined threshold. Note that, the threshold of the color ratio G/R used here is preferably set strictly (smaller value) relative to the determination criteria (color ratio G/R) used for detection of the abnormal regions in step S11.

Generally, when bleeding occurs in a lumen, blood flows from an upstream side (oral cavity side) to a downstream side (anus side). Therefore, it can be considered that a bleeding source is shown in an abnormal image captured at an imaging position on the most upstream side of abnormal images including an abnormal region having a strong reddish color.

In the following step S214, the representative-image extracting unit 141 extracts, as the representative image, one of the bleeding source images detected in step S213.

In the following step S215, the representative-image extracting unit 141 extracts n−1 representative images at random from abnormal images (excluding the bleeding source image) including abnormal regions having a strong reddish color of the abnormal image group, where n is the number of representative images to be extracted.

In the following step S216, the representative-image extracting unit 141 determines whether n representative images can be extracted. When the abnormal image group has at least n abnormal images including the abnormal regions having a strong reddish color, a total of n representative images can be extracted from the at least n abnormal images. In this condition (step S216: Yes), the process proceeds to step S219.

In contrast, when the abnormal images including the abnormal regions having a strong reddish color is less than n, in the abnormal image group, n representative images cannot be extracted. In this condition (step S216: No), the representative-image extracting unit 141 extracts representative images at random from the remaining abnormal images not including the abnormal regions having a strong reddish color, until a total n representative images are extracted (step S217). Then, the process proceeds to step S219.

Furthermore, in step S211, when identical abnormal regions in an abnormal image group to be processed do not have the bleeding (step S211: No), the representative-image extracting unit 141 extracts n representative images from the abnormal image group, similarly to the first embodiment (step S218). Then, the process proceeds to step S219.

In step S219, the representative-image extracting unit 141 adds information (flag) indicating the representative image to image data of the extracted n representative images.

After completion of processing of the loop B for all abnormal image groups extracted in step S23 (see FIG. 8), operation of the image processing apparatus returns to a main routine.

As described above, according to modification 2, based on the intensity of the reddish color of the abnormal region and the positional information of each abnormal image in a lumen, a bleeding source having a high degree of importance can be preferentially extracted as the representative image, in diagnosis.

Third Embodiment

Next, a third embodiment of the present invention will be described.

Figure 13:
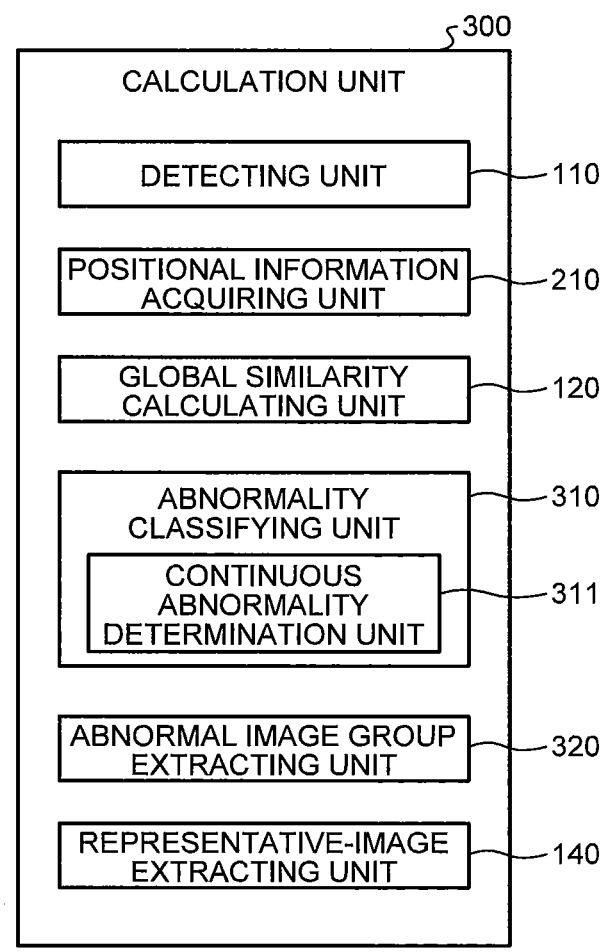
FIG. 13 is a block diagram illustrating a configuration of a calculation unit of an image processing apparatus according to a third embodiment of the present invention.

FIG. 13 is a block diagram illustrating a configuration of a calculation unit of an image processing apparatus according to the third embodiment of the present invention. The image processing apparatus according to the third embodiment includes a calculation unit 300 illustrated in FIG. 13, instead of the calculation unit 100 illustrated in FIG. 1. Configurations and operations of units other than the calculation unit 300 are similar to those of the first embodiment.

The calculation unit 300 includes the detecting unit 110, the positional information acquiring unit 210, the global similarity calculating unit 120, an abnormality classifying unit 310, an abnormal image group extracting unit 320, and the representative-image extracting unit 140. Among these, operations of the detecting unit 110, the global similarity calculating unit 120, and the representative-image extracting unit 140 are similar to those of the first embodiment. Furthermore, operation of the positional information acquiring unit 210 is similar to that of the second embodiment.

The abnormality classifying unit 310 is a region-of-interest classifying unit for classifying abnormal regions as regions of interest, according to types of a subject in the abnormal regions. Specifically, the abnormality classifying unit 310 includes a continuous abnormality determination unit (continuity determination unit) 311 for determining whether the abnormal regions occur continuously in the series of intraluminal images. if the subject in the abnormal regions is an abnormality such as floating blood or vascular abnormality, the continuous abnormality determination unit 311 determines that the abnormal regions occur continuously.

Kinds of abnormality such as floating blood or vascular abnormality can be determined using determination criteria previously developed. The determination criteria are developed by a learning tool such as a support vector machine (SVM), based on a feature distribution of an abnormal region such as floating blood or vascular abnormality shown in an intraluminal image, and stored in the recording unit 50. The feature includes color features (values of R component, G component, and B component of a pixel value, values secondarily calculated by known conversion based on the values of these color components (color difference calculated by YCbCr conversion, hue or saturation calculated by HSI conversion, color ratio such as G/R or B/G, or the like)), shape features (shape information such as HOG, area, circumferential length, or Feret's diameter), and texture features (LBP, simultaneous normal matrix, or the like).

The abnormal image group extracting unit 320 extracts abnormal image groups each including identical abnormal regions, based on the positional information acquired by the positional information acquiring unit 210, the global similarity calculated by the global similarity calculating unit 120, and a classification result by the abnormality classifying unit 310.

Figure 14:
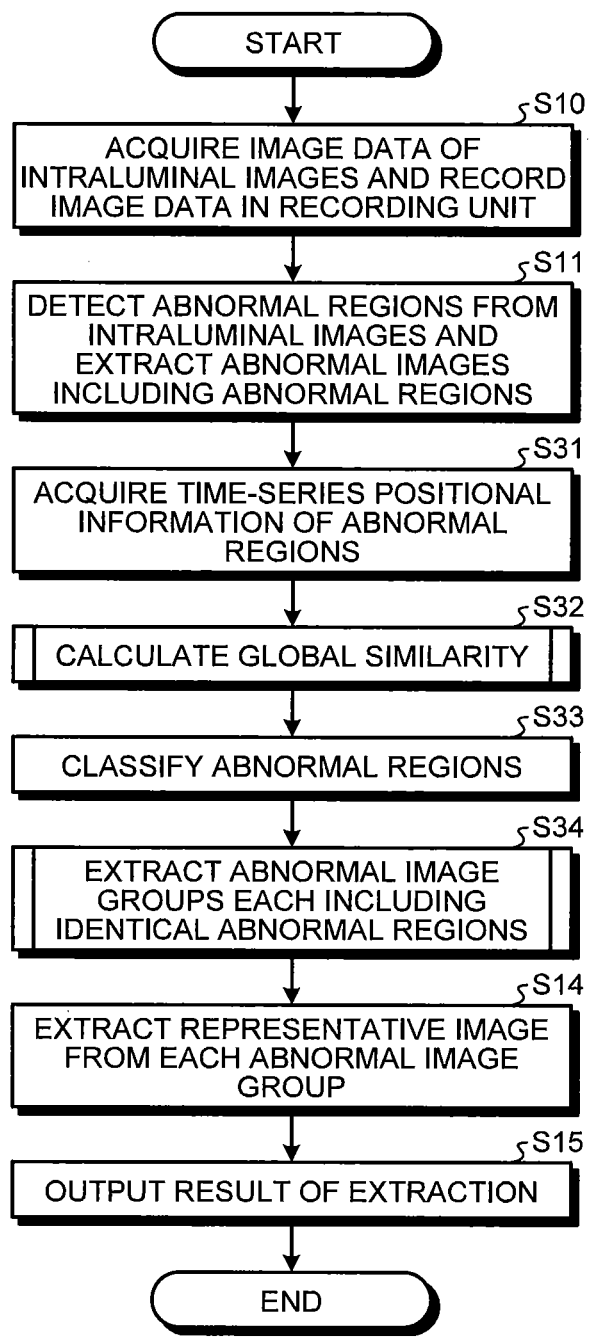
FIG. 14 is a flowchart illustrating operation of the image processing apparatus according to the third embodiment of the present invention.

Next, operation of the image processing apparatus according to the third embodiment will be described. FIG. 14 is a flowchart illustrating operation of the image processing apparatus according to the third embodiment. Note that, steps S10 and S11 illustrated in FIG. 14 are similar to those of the first embodiment (see FIG. 2).

In step S31 subsequent to step S11, the positional information acquiring unit 210 acquires time-series positional information of the abnormal images extracted in step S11. Specifically, an arrangement order i or imaging time of the abnormal image $I_i$ is acquired as the positional information.

In the following step S32, the global similarity calculating unit 120 calculates the global similarity between adjacent abnormal images in an abnormal image sequence. A method for calculating the global similarity is similar to that described in the first embodiment (see FIGS. 4 and 5). Alternatively, the global similarity may be calculated in a similar manner to modifications 1-1 to 1-3.

In the following step S33, the abnormality classifying unit 310 classifies each of the abnormal regions detected in step S11. Specifically, the continuous abnormality determination unit 311 reads determination criteria for determining the abnormal regions occurring continuously, from the recording unit 50, compares features calculated for abnormal regions to be processed with the determination criteria to determine the types of a subject in the abnormal regions, and determines, according to the types of the subject, whether the abnormal regions occur continuously. Specifically, if the subject in the abnormal regions is floating blood or vascular abnormality, the abnormal regions are determined to be occurring continuously.

In the following step S34, the abnormal image group extracting unit 320 uses the positional information acquired in step S31 and the global similarity calculated in step S32, based on a result of the classification in step S33, and extracts abnormal image groups each including identical abnormal regions.

Figure 15:
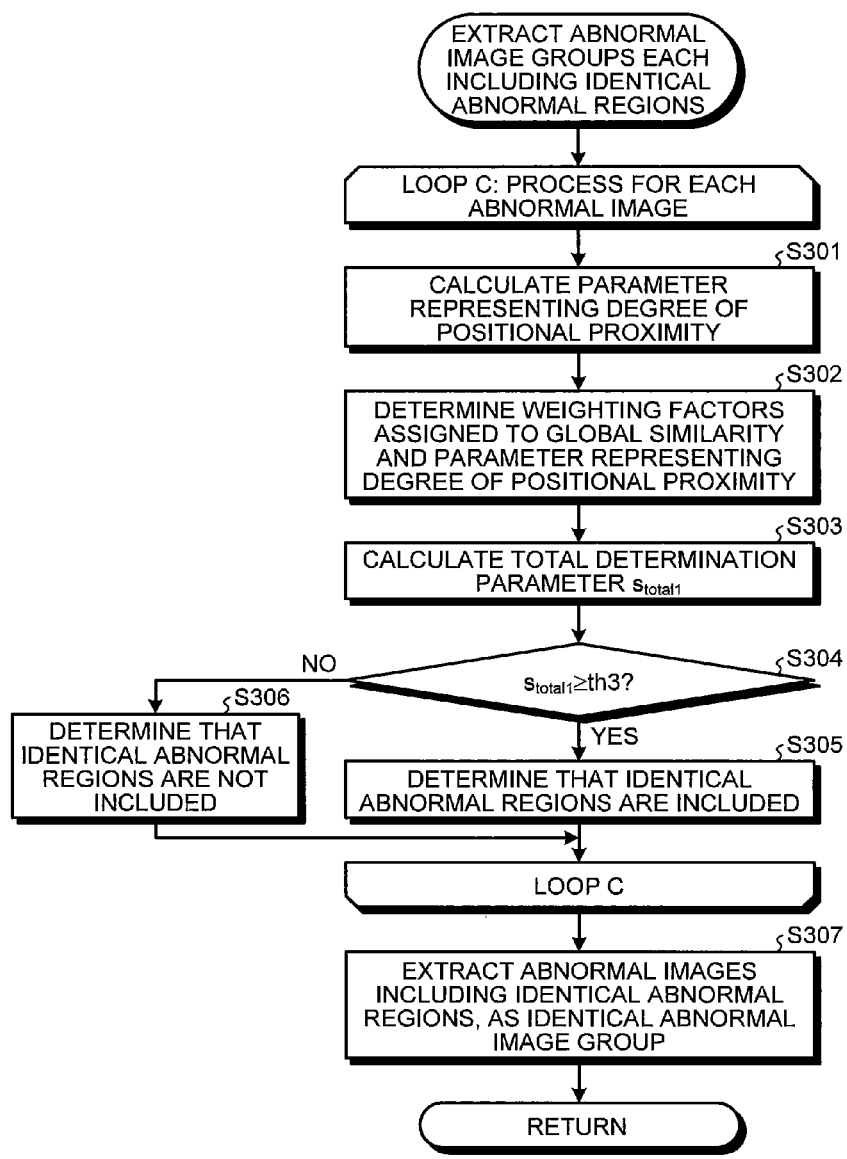
FIG. 15 is a flowchart illustrating an abnormal image group extraction process performed by an abnormal image group extracting unit illustrated in FIG. 13.

FIG. 15 is a flowchart illustrating an abnormal image group extraction process performed by the abnormal image group extracting unit 320 in step S34. The abnormal image group extracting unit 320 performs processing of a loop C for each abnormal image extracted in step S11.

First, in step S301, the abnormal image group extracting unit 320 calculates a parameter $s_{pos}$ representing a degree of positional proximity between an abnormal image $I_j$ (j is a natural number) to be processed, and an abnormal image $I_{j+n}$ (n is a natural number) adjacent to the abnormal image $I_j$ in an abnormal image sequence. The parameter $s_{pos}$ is given by the following formula (2).

$$s_{pos} = (N-n)/N \quad (2)$$

In formula (2), N is a parameter for normalizing a difference n in arrangement order, and for example set to N=10. This parameter $s_{pos}$ has a larger value, when the subjects shown in the abnormal images $I_j$ and $I_{j+n}$ are closer in position in a lumen (when n is smaller).

Note that, in step S31, when imaging time of the abnormal image $I_t$ is acquired as the positional information, a difference between imaging time is substituted for the difference n in arrangement order, in formula (2), and a parameter for normalizing the difference between imaging time is used for the parameter N to calculate the parameter representing the degree of positional proximity.

In the following step S302, the abnormal image group extracting unit 320 determines weighting factors $w_1$ and $w_2$ ($w_1+w_2=1$) assigned to the global similarity $s_{global}$ and the parameter $s_{pos}$ representing the degree of positional proximity, respectively, based on a result of the classification of the abnormal regions in the abnormal images to be processed (see step S33). At this time, if the abnormal image $I_j$ has an abnormal region occurring continuously, the weighting factors $w_1$ and $w_2$ are determined so that the weighting factor $w_2$ is larger relative to the weighting factor $w_1$. In contrast, if the abnormal image $I_j$ has an abnormal region that does not continuously occur, the weighting factors $w_1$ and $w_2$ are determined such that the weighting factor $w_1$ is larger relative to the weighting factor $w_2$.

In the following step S303, the abnormal image group extracting unit 320 uses the weighting factors $w_1$ and $w_2$ determined in step S302 to calculate a total determination parameter $s_{total1}$ to which the global similarity $s_{global}$ and the parameter $s_{pos}$ representing the degree of positional proximity are added. The total determination parameter $s_{total1}$ is given by the following formula (3).

$$s_{total1} = w_1 \cdot s_{global} + w_2 \cdot s_{pos} \quad (3)$$

In the following step S304, the abnormal image group extracting unit 320 determines whether the total determination parameter $s_{total1}$ is not less than a predetermined threshold th3. When the total determination parameter $s_{total1}$ is not less than the threshold th3 (step S304: Yes), the abnormal image group extracting unit 320 determines that the abnormal image $I_j$ to be processed and the abnormal image $I_{j+n}$ extracted subsequent to the abnormal image $I_j$ include identical abnormal regions (step S305). In contrast, when the total determination parameter $s_{total}$ is less than the threshold th3 (step S304: No), the abnormal image group extracting unit 320 determines that the abnormal image $I_j$ to be processed and the abnormal image $I_{j+n}$ extracted subsequent to the abnormal image $I_j$ do not include identical abnormal regions (step S306).

After completion of the processing of the loop C for all abnormal images, the abnormal image group extracting unit 320 extracts abnormal images determined to show identical abnormal regions, as the identical abnormal image group, in step S307. Then, operation of the image processing apparatus returns to a main routine.

Steps S14 and S15 subsequent to step S34 are similar to those of the first embodiment (see FIG. 2).

As described above, according to the third embodiment of the present invention, when the abnormal image group including identical abnormal regions is extracted, based on the time-series positional information and the global similarity of an abnormal image, the weighting factors of the global similarity and the positional information are changed depending on whether the abnormal region in the abnormal image occurs continuously, and thus, accuracy in extraction of the abnormal image group including identical abnormal regions can be increased.

Modification 3-1

Next, modification 3-1 of the third embodiment of the present invention will be described.

Figure 16:
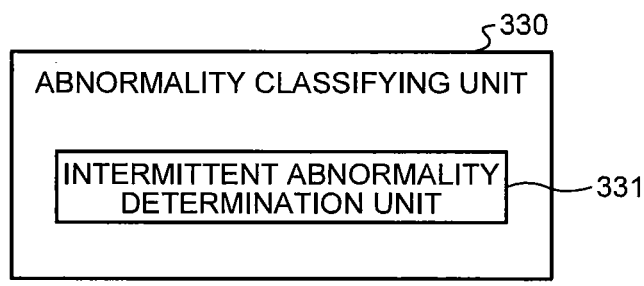
FIG. 16 is a block diagram illustrating another exemplary configuration of an abnormality classifying unit illustrated in FIG. 13.

FIG. 16 is a block diagram illustrating another exemplary configuration of an abnormality classifying unit 310 illustrated in FIG. 13. In the calculation unit 300 illustrated in FIG. 13, an abnormality classifying unit 330 illustrated in FIG. 16 may be provided instead of the abnormality classifying unit 310. The abnormality classifying unit 330 includes an intermittent abnormality determination unit (intermittency determination unit) 331 for determining whether an abnormal region occurs intermittently in the series of intraluminal images. If a subject in an abnormal region is abnormality such as redness, bleeding point, aphtha, or ulcer, the intermittent abnormality determination unit 331 determines that the abnormal region occurs intermittently.

The kinds of abnormality such as redness, bleeding point, aphtha, or ulcer can be determined using determination criteria previously developed. The determination criteria are developed by a learning tool such as a support vector machine (SVM), based on a feature distribution of an abnormal region such as redness, bleeding point, aphtha, ulcer shown in an intraluminal image, and stored in the recording unit 50. The feature includes color features (values of R component, G component, and B component of a pixel value, values secondarily calculated by known conversion based on the values of these color components (color difference calculated by YCbCr conversion, hue or saturation calculated by HSI conversion, color ratio such as G/R or B/G, or the like)), shape features (shape information such as HOG, area, circumferential length, or Feret's diameter), and texture features (LBP, simultaneous normal matrix, or the like).

In this configuration, in step S33 illustrated in FIG. 14, the abnormality classifying unit 330 classifies the abnormal regions detected in step S11. Specifically, the intermittent abnormality determination unit 331 reads determination criteria for determining the abnormal regions occurring intermittently, from the recording unit 50, compares features calculated for abnormal regions to be processed with the determination criteria to determine the types of a subject in the abnormal regions, and determines, according to the types of the subject, whether the abnormal regions occur intermittently.

Furthermore, in this configuration, in step S34 illustrated in FIG. 14, the abnormal image group extracting unit 320 uses the positional information acquired in step S31 and the global similarity calculated in step S32, based on a result of the classification by the abnormality classifying unit 330, and extracts abnormal image groups each including identical abnormal regions.

Specifically, in step S302 illustrated in FIG. 15, the abnormal image group extracting unit 320 determines the weighting factors $w_1$ and $w_2$ assigned to the global similarity $s_{global}$ and the parameter $s_{pos}$ representing the degree of positional proximity, based on a result of the classification of the abnormal regions by the abnormality classifying unit 330. At this time, if the abnormal image $I_j$ has an abnormal region that occurs intermittently, the weighting factors $w_1$ and $w_2$ are determined so that the weighting factor $w_1$ is larger relative to the weighting factor $w_2$. In contrast, if the abnormal image $I_j$ has an abnormal region that does not intermittently occur, the weighting factors $w_1$ and $w_2$ are determined so that the weighting factor $w_2$ is larger relative to the weighting factor $w_1$.

Modification 3-2

Next, modification 3-2 of the third embodiment of the present invention will be described.

Figure 17:
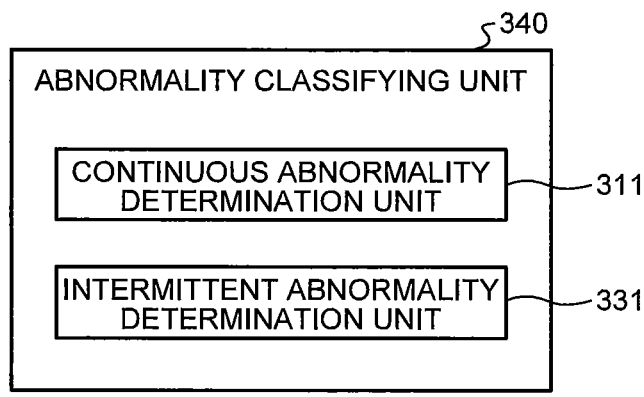
FIG. 17 is a block diagram illustrating still another exemplary configuration of the abnormality classifying unit illustrated in FIG. 13.

FIG. 17 is a block diagram illustrating still another exemplary configuration of the abnormality classifying unit 310 illustrated in FIG. 13. In the calculation unit 300 illustrated in FIG. 13, an abnormality classifying unit 340 illustrated in FIG. 17 may be provided instead of the abnormality classifying unit 310. The abnormality classifying unit 340 includes the continuous abnormality determination unit 311 and the intermittent abnormality determination unit 331. Operation of the continuous abnormality determination unit 311 is similar to that of the third embodiment, and operation of the intermittent abnormality determination unit 331 is similar to that of modification 3-1.

In this configuration, in step S33 illustrated in FIG. 14, the abnormality classifying unit 340 classifies the abnormal regions detected in step S11. Specifically, the continuous abnormality determination unit 311 determines whether abnormal regions to be processed occur continuously in a group of a series of intraluminal images. The intermittent abnormality determination unit 331 determines whether abnormal regions to be processed occur intermittently in the group of a series of intraluminal images. In consequence, the abnormal regions are classified into the abnormal region occurring continuously, the abnormal region occurring intermittently, and the other abnormal regions.

In this configuration, in step S34 illustrated in FIG. 14, the abnormal image group extracting unit 320 uses the positional information acquired in step S31 and the global similarity calculated in step S32, based on a result of the classification by the abnormality classifying unit 340, and extracts abnormal image groups each including identical abnormal regions.

Specifically, in step S302 illustrated in FIG. 15, the abnormal image group extracting unit 320 determines the weighting factors $w_1$ and $w_2$ assigned to the global similarity $s_{global}$ and the parameter $s_{pos}$ representing the degree of positional proximity, respectively, based on a result of the classification by the abnormality classifying unit 340. At this time, if the abnormal image $I_j$ has an abnormal region that occurs continuously, the weighting factors $w_1$ and $w_2$ are determined so that the weighting factor $w_2$ is larger relative to the weighting factor $w_1$. In contrast, if the abnormal image $I_j$ has an abnormal region that occurs intermittently, the weighting factors $w_1$ and $w_2$ are determined so that the weighting factor $w_1$ is larger relative to the weighting factor $w_2$. Furthermore, if the abnormal image $I_j$ has an abnormal region that does not continuously occur or intermittently occur, the weighting factors $w_1$ and $w_2$ are determined to be equal.

Fourth Embodiment

Next, a fourth embodiment of the present invention will be described.

Figure 18:
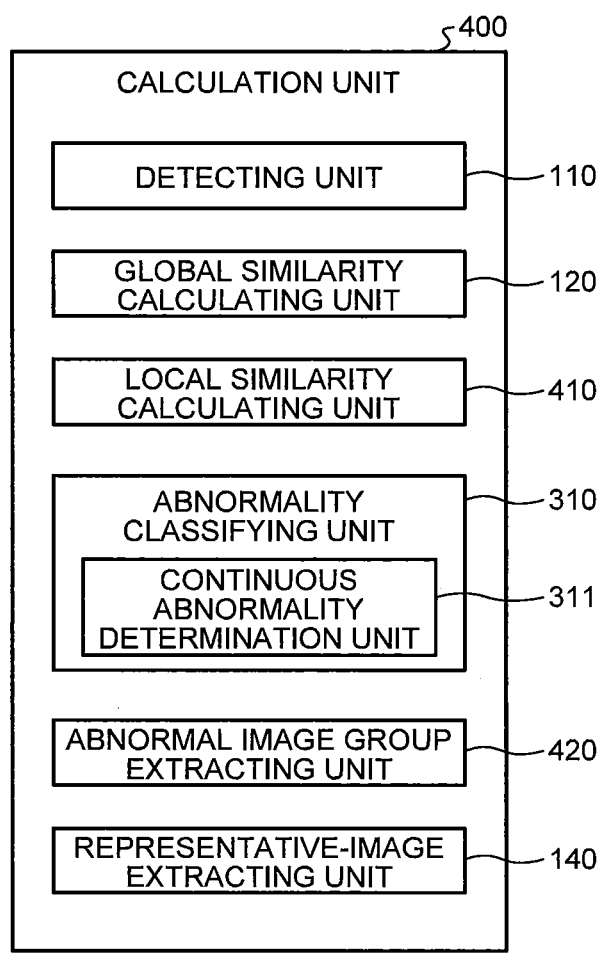
FIG. 18 is a block diagram illustrating a configuration of a calculation unit of an image processing apparatus according to a fourth embodiment of the present invention.

FIG. 18 is a block diagram illustrating a configuration of a calculation unit of an image processing apparatus according to the fourth embodiment of the present invention. The image processing apparatus according to the fourth embodiment includes a calculation unit 400 illustrated in FIG. 18, instead of the calculation unit 100 illustrated in FIG. 1. Configurations and operations of units other than the calculation unit 400 are similar to those of the first embodiment.

The calculation unit 400 includes the detecting unit 110, the global similarity calculating unit 120, a local similarity calculating unit 410, the abnormality classifying unit 310, an abnormal image group extracting unit 420, and the representative-image extracting unit 140. Among these, operations of the detecting unit 110, the global similarity calculating unit 120, and the representative-image extracting unit 140 are similar to those of the first embodiment (see FIG. 1). Furthermore, operation of the abnormality classifying unit 310 is similar to that of the third embodiment.

The local similarity calculating unit 410 calculates, as a local similarity, a similarity between abnormal regions between adjacent abnormal images in an abnormal image sequence.

The abnormal image group extracting unit 420 extracts abnormal image groups each including identical abnormal regions, based on the global similarity calculated by the global similarity calculating unit 120, the local similarity calculated by the local similarity calculating unit 410, and a result of the classification by the abnormality classifying unit 310.

Figure 19:
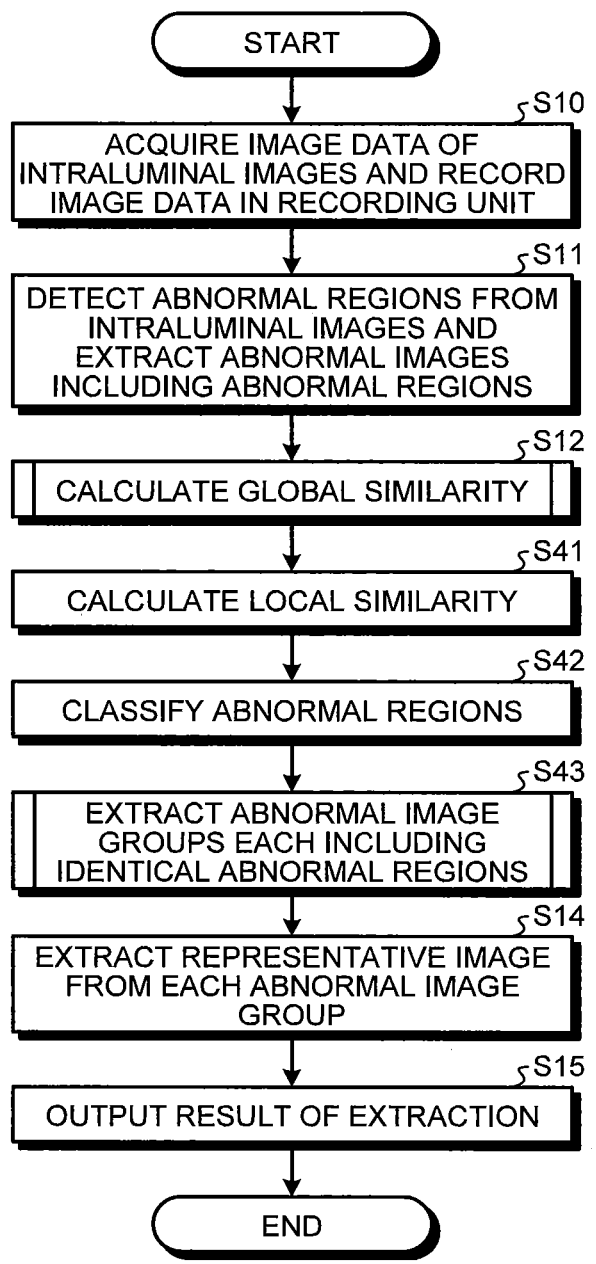
FIG. 19 is a flowchart illustrating operation of the image processing apparatus according to the fourth embodiment of the present invention.

Next, operation of the image processing apparatus according to the fourth embodiment will be described. FIG. 19 is a flowchart illustrating operation of the image processing apparatus according to the fourth embodiment. Note that, steps S10 to S12 illustrated in FIG. 19 are similar to those of the first embodiment (see FIG. 2). In step S12, the global similarity may be calculated in a similar manner to modifications 1-1 to 1-3.

In step S41 subsequent to step S12, the local similarity calculating unit 410 calculates the local similarity between adjacent abnormal images in an abnormal image sequence. A local similarity calculation method is not particularly limited. As an example, when corresponding points are extracted between abnormal images by a known method such as scale invariant feature transform (SIFT), and abnormal regions correspond to each other between two abnormal images, the local similarity is defined to be 1.0. In contrast, abnormal regions do not correspond to each other between two abnormal images, the local similarity is defined to be 0.0.

In the following step S42, the abnormality classifying unit 310 classifies each of the abnormal regions detected in step S11. That is, the continuous abnormality determination unit 311 reads determination criteria for determining abnormal regions occurring continuously, from the recording unit 50 to determine whether the abnormal regions occur continuously, based on the determination criteria.

In the following step S43, the abnormal image group extracting unit 420 uses the global similarity calculated in step S12 and the local similarity calculated in step S41, based on a result of the classification in step S42, and extracts abnormal image groups each including identical abnormal regions.

Figure 20:
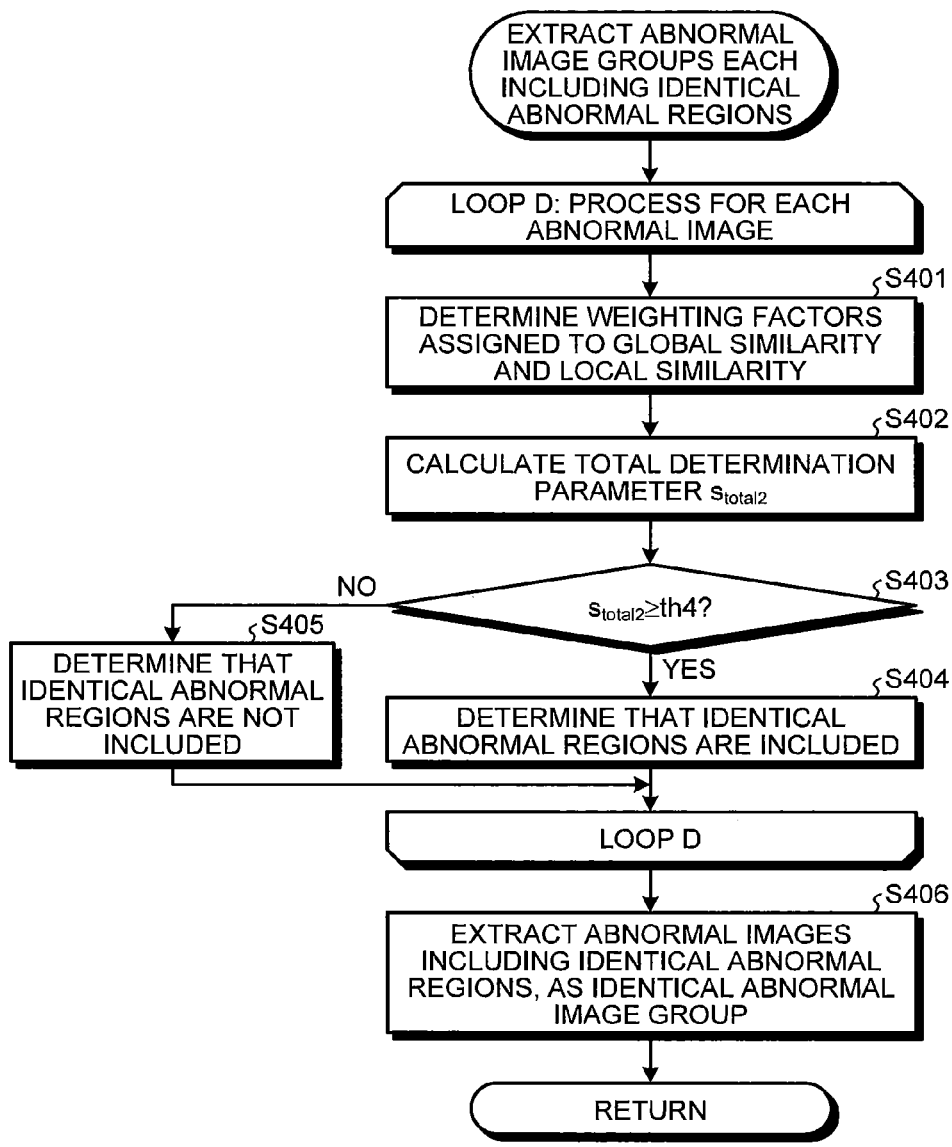
FIG. 20 is a flowchart illustrating an abnormal image group extraction process performed by an abnormal image group extracting unit illustrated in FIG. 18.

FIG. 20 is a flowchart illustrating an abnormal image group extraction process performed by the abnormal image group extracting unit 420 in step S43. The abnormal image group extracting unit 420 performs processing of a loop D for each abnormal image extracted in step S11.

First, in step S401, the abnormal image group extracting unit 420 determines weighting factors $w_3$ and $w_4$ assigned to the global similarity $s_{global}$ and a local similarity $s_{local}$, respectively, based on a result of the classification of the abnormal regions in the abnormal images to be processed (see step S42). If the abnormal regions occur continuously, the weighting factors $w_3$ and $w_4$ are determined so that the weighting factor $w_3$ is relatively larger (e.g., $w_3=1$, $w_4=0$, etc.). In contrast, if the abnormal regions do not continuously occur, the weighting factors $w_3$ and $w_4$ are determined so that the weighting factor $w_4$ is relatively larger (e.g., $w_3=0$, $w_4=1$, etc.).

In the following step S402, the abnormal image group extracting unit 420 uses the weighting factors $w_3$ and $w_4$ determined in step S401, to calculate a total determination parameter $s_{total2}$ to which the global similarity $s_{global}$ and the local similarity $s_{local}$ are added. The total determination parameter $s_{total2}$ is given by the following formula (4).

$$s_{total2} = w_3 \cdot s_{global} + w_4 \cdot s_{local} \tag{4}$$

In the following step S403, the abnormal image group extracting unit 420 determines whether the total determination parameter $s_{total2}$ is not less than a predetermined threshold th4. When the total determination parameter $s_{total2}$ is not less than the threshold th4 (step S403: Yes), the abnormal image group extracting unit 420 determines that an abnormal image to be processed and an abnormal image extracted subsequent to the abnormal image include identical abnormal regions (step S404). In contrast, when the total determination parameter $s_{total2}$ is less than the threshold th4 (step S403: No), the abnormal image group extracting unit 420 determines that an abnormal image to be processed and an abnormal image extracted subsequent to the abnormal image do not include identical abnormal regions (step S405).

After completion of the processing of the loop D for all abnormal images, the abnormal image group extracting unit 420 extracts abnormal images determined to show identical abnormal regions, as the identical abnormal image group, in step S406. Then, operation of the image processing apparatus returns to a main routine.

Note that, steps S14 and S15 subsequent to step S43 are similar to those of the first embodiment (see FIG. 2).

As described above, according to the fourth embodiment of the present invention, the weighting factors assigned to the overall similarity between abnormal images and the local similarity between abnormal regions, respectively, are changed depending on whether an abnormal region occurs continuously, and it is determined whether two abnormal images include identical abnormal regions thereof, based on the total determination parameter thereof. Thus, accuracy in extraction of an abnormal image group including identical abnormal regions can be increased.

Modification 4-1

Next, modification 4-1 of the fourth embodiment of the present invention will be described.

The local similarity calculating unit 410 illustrated in FIG. 18 may calculate the local similarity using various methods, in addition to the method described in the fourth embodiment.

As an example, the local similarity calculating unit 410 calculates features of abnormal regions included in the abnormal images, first. The features include for example a statistic such as an average value, median, or the like of pixel values (luminance values or G component values) of pixels constituting the abnormal regions, a statistic such as an average value, median, or the like of color features (color difference calculated by YCbCr conversion, hue or saturation calculated by HSI conversion, a color ratio such as G/R or B/G, or the like, using R component, G component, and B component values) of pixels constituting the non-abnormal regions, and a statistic such as an average value, median, or the like of shape features (areas, circularity, or the like) of the abnormal regions, or texture features (edge amounts or the like calculated using Sobel filter, Laplacian filter, or the like) in pixels constituting the abnormal regions.

Next, the local similarity calculating unit 410 calculates an amount of change $\Delta c_a$ in feature described above, between adjacent abnormal images in an abnormal image sequence. Then, a maximum value $c_{a(max)}$ and the amount of change $\Delta c_a$ in feature are used to calculate the local similarity $s_{local}$ given by the following formula (5).

$$s_{local} = (c_{a(max)} - \Delta c_a)/c_{a(max)} \tag{5}$$

In formula (5), the maximum value $c_{a(max)}$ in features is a maximum value taken by the features. For example, when statistical values of pixel values (G component values) are calculated as the features, for the abnormal images having 256 tone levels, the features have a maximum value $c_{a(max)}$ of 256. Furthermore, when circularity is calculated as the features, the circularity has a maximum value $c_{a(max)}$ of 1.

Modification 4-2

Next, modification 4-2 of the fourth embodiment of the present invention will be described.

In the calculation unit 400 illustrated in FIG. 18, instead of the abnormality classifying unit 310, the abnormality classifying unit 330 only including the intermittent abnormality determination unit 331 illustrated in FIG. 16 may be provided to classify the abnormal regions to be processed, into two abnormal regions, that is, the abnormal regions occurring intermittently and the other abnormal regions (see Modification 3-1).

In this configuration, in step S42 illustrated in FIG. 19, the abnormality classifying unit 330 classifies the abnormal regions detected in step S11. That is, the intermittent abnormality determination unit 331 reads determination criteria for determining abnormal regions occurring intermittently, from the recording unit 50 to determine whether the abnormal regions occur intermittently, based on the determination criteria.

Furthermore, in this configuration, in step S43 illustrated in FIG. 19, the abnormal image group extracting unit 420 uses the global similarity $s_{global}$ calculated in step S12 and the local similarity $s_{local}$ calculated in step S41, based on a result of the classification by the abnormality classifying unit 330, and extracts abnormal image groups each including identical abnormal regions.

Specifically, in step S401 illustrated in FIG. 20, the abnormal image group extracting unit 420 determines the weighting factors $w_3$ and $w_4$ assigned to the global similarity $s_{global}$ and the local similarity $s_{local}$, based on a result of the classification of the abnormal regions by the abnormality classifying unit 330. If the abnormal regions occur intermittently, the weighting factors $w_3$ and $w_4$ are determined so that the weighting factor $w_4$ is relatively larger (e.g, $w_3=0$, $w_4=1$, etc.). In contrast, if the abnormal regions do not intermittently occur, the weighting factors $w_3$ and $w_4$ are determined so that the weighting factor $w_3$ is relatively larger (e.g., $w_3=1$, $w_4=0$, etc.).

Modification 4-3

Next, modification 4-3 of the fourth embodiment of the present invention will be described.

In the calculation unit 400 illustrated in FIG. 18, instead of the abnormality classifying unit 310, the abnormality classifying unit 340 including the continuous abnormality determination unit 311 and the intermittent abnormality determination unit 331 illustrated in FIG. 17 may be provided to classify the abnormal regions to be processed, into three abnormal regions, that is, the abnormal regions occurring continuously, the abnormal regions occurring intermittently, and the other abnormal regions (see Modification 3-2).

In this configuration, in step S42 illustrated in FIG. 19, the abnormality classifying unit 340 classifies the abnormal regions detected in step S11. That is, the continuous abnormality determination unit 311 determines whether abnormal regions to be processed occur continuously in the group of a series of intraluminal images. The intermittent abnormality determination unit 331 determines whether abnormal regions to be processed occur intermittently in the group of a series of intraluminal images.

In this configuration, in step S43 illustrated in FIG. 19, the abnormal image group extracting unit 420 uses the global similarity $s_{global}$ calculated in step S12 and the local similarity $s_{local}$ calculated in step S41, based on a result of the classification by the abnormality classifying unit 340, and extracts abnormal image groups each including identical abnormal regions.

Specifically, in step S401 illustrated in FIG. 20, the abnormal image group extracting unit 420 determines the weighting factors $w_3$ and $w_4$ assigned to the global similarity $s_{global}$ and the local similarity $s_{local}$, respectively, based on a result of the classification by the abnormality classifying unit 340. If the abnormal regions occur continuously, the weighting factors $w_3$ and $w_4$ are determined so that the weighting factor $w_3$ is relatively larger (e.g., $w_3=1$, $w_4=0$, etc.). If the abnormal regions occur intermittently, the weighting factors $w_3$ and $w_4$ are determined so that the weighting factor $w_4$ is relatively larger (e.g., $w_3=0$, $w_4=1$, etc.). Furthermore, if the abnormal regions do not continuously occur or intermittently occur, the weighting factors $w_3$ and $w_4$ are determined to have an equal value (e.g., $w_3=0.5$, $w_4=0.5$, etc.).

Fifth Embodiment

Next, a fifth embodiment of the present invention will be described.

Figure 21:
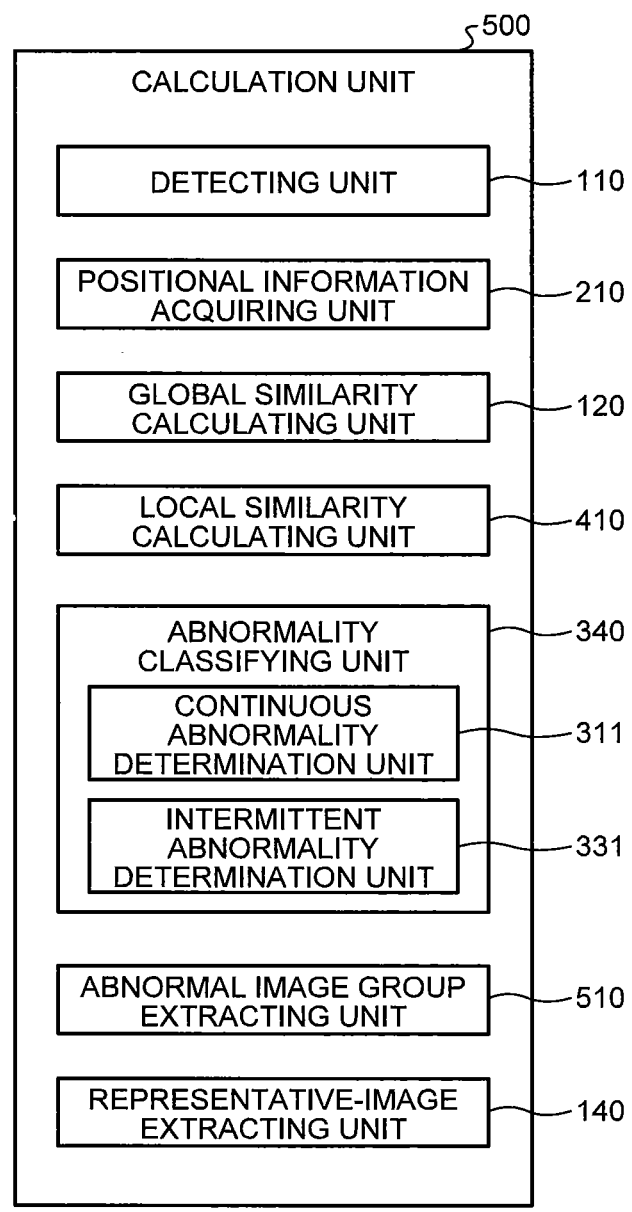
FIG. 21 is a block diagram illustrating a configuration of a calculation unit of an image processing apparatus according to a fifth embodiment of the present invention.

FIG. 21 is a block diagram illustrating a configuration of a calculation unit of an image processing apparatus according to the fifth embodiment of the present invention. The image processing apparatus according to the fifth embodiment includes a calculation unit 500 illustrated in FIG. 21, instead of the calculation unit 100 illustrated in FIG. 1. Configurations and operations of units other than the calculation unit 500 are similar to those of the first embodiment.

The calculation unit 500 includes the detecting unit 110, the positional information acquiring unit 210, the global similarity calculating unit 120, the local similarity calculating unit 410, the abnormality classifying unit 340, an abnormal image group extracting unit 510, and the representative-image extracting unit 140. Among these, operations of the detecting unit 110, the global similarity calculating unit 120, and the representative-image extracting unit 140 are similar to those of the first embodiment (see FIG. 1). Operation of the positional information acquiring unit 210 is similar to that of the second embodiment. (see FIG. 7). Operation of the local similarity calculating unit 410 is similar to that of the fourth embodiment or modification 4-1 (see FIG. 18). Operation of the abnormality classifying unit 340 is similar to that of modification 3-2 (see FIG. 17).

The abnormal image group extracting unit 510 extracts abnormal image groups each including identical abnormal regions, based on the positional information acquired by the positional information acquiring unit 210, the global similarity calculated by the global similarity calculating unit 120, the local similarity calculated by the local similarity calculating unit 410, and a result of the classification by the abnormality classifying unit 340.

Figure 22:
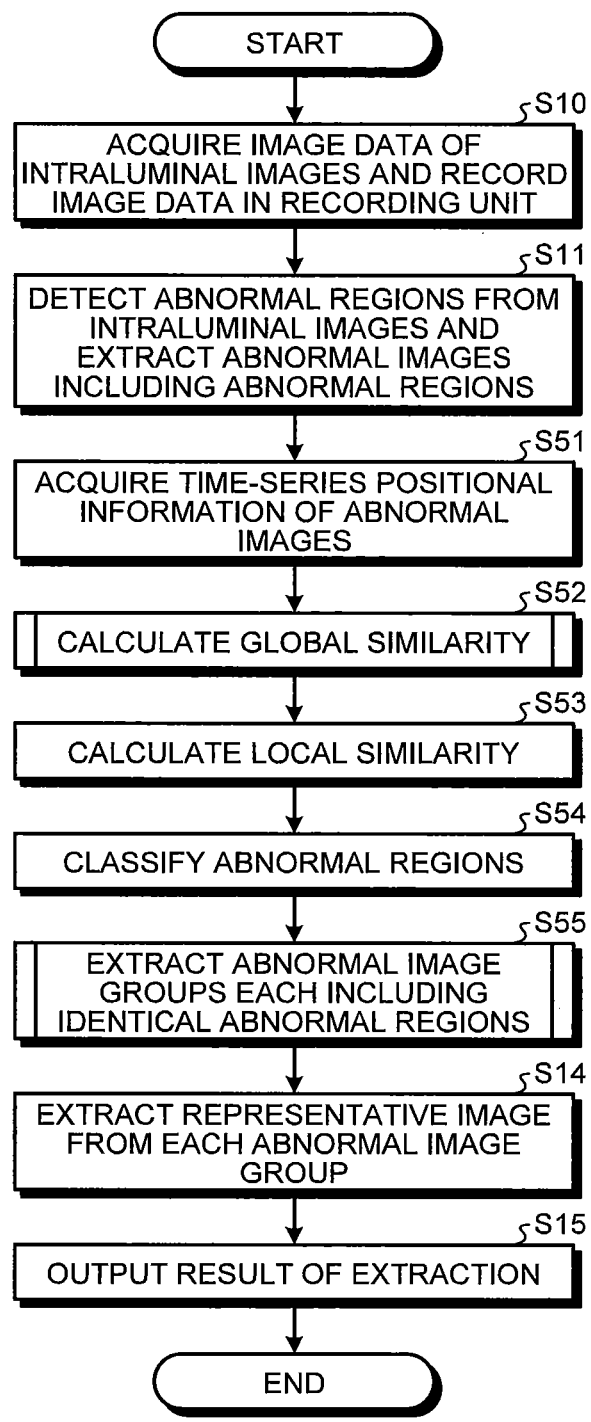
FIG. 22 is a flowchart illustrating operation of the image processing apparatus according to the fifth embodiment of the present invention.

Next, operation of the image processing apparatus according to the fifth embodiment will be described. FIG. 22 is a flowchart illustrating operation of the image processing apparatus according to the fifth embodiment. Note that, steps S10 and S11 illustrated in FIG. 14 are similar to those of the first embodiment (see FIG. 2).

In step S51 subsequent to step S11, the positional information acquiring unit 210 acquires, as the time-series positional information of the abnormal images extracted in step S11, the imaging time or the arrangement order i of the abnormal images $I_i$.

In the following step S52, the global similarity calculating unit 120 calculates the global similarity $s_{global}$ between adjacent abnormal images in an abnormal image sequence. A method for calculating the global similarity $S_{global}$ is similar to that described in the first embodiment (see FIGS. 4 and 5). Alternatively, the global similarity $s_{global}$ may be calculated in a similar manner to modifications 1-1 to 1-3.

In the following step S53, the local similarity calculating unit 410 calculates the local similarity $s_{local}$ between adjacent abnormal images in an abnormal image sequence. A method for calculating the local similarity $S_{local}$ is similar to that described in the fourth embodiment or modification 4-1 (see step S41 of FIG. 19).

In the following step S54, the abnormality classifying unit 340 classifies each of the abnormal regions detected in step S11. A method for classifying the abnormal regions is similar to that described in modification 3-2. In consequence, the abnormal regions are classified into the abnormal regions occurring continuously, the abnormal regions occurring intermittently, and the other abnormal regions.

In the following step S55, the abnormal image group extracting unit 510 extracts abnormal image groups each including identical abnormal regions, according to the positional information acquired in step S51, the global similarity $s_{global}$ calculated in step S52, and the local similarity $s_{local}$ calculated in step S53, based on a result of the classification in step S54.

Figure 23:
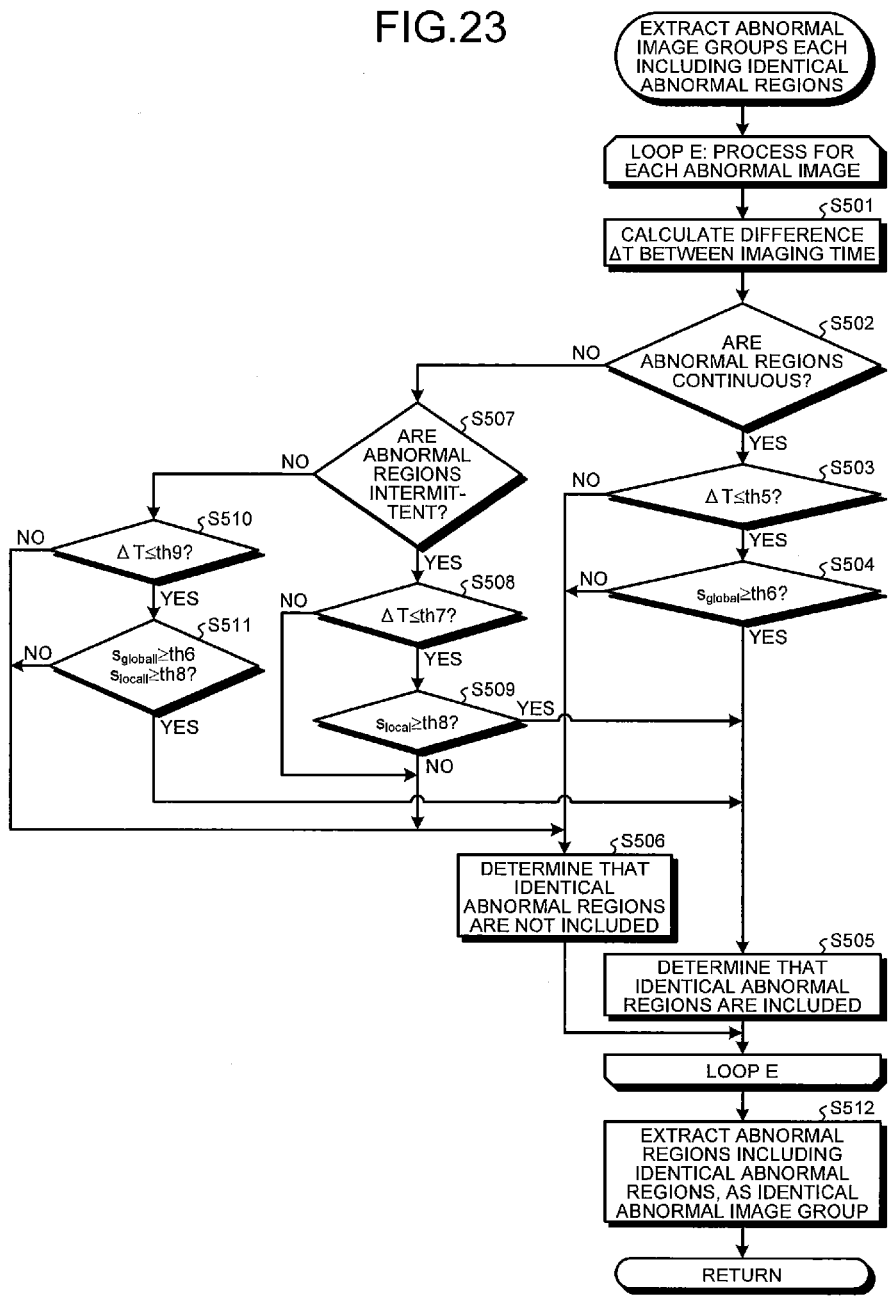
FIG. 23 is a flowchart illustrating an abnormal image group extraction process performed by an abnormal image group extracting unit illustrated in FIG. 21.

FIG. 23 is a flowchart illustrating an abnormal image group extraction process performed by the abnormal image group extracting unit 510 in step S55. The abnormal image group extracting unit 510 performs processing of a loop E for each abnormal image extracted in step S11.

First, in step S501, the abnormal image group extracting unit 510 calculates a difference $\Delta T$ ($=T(I_{k'})-T(I_k)$) between imaging time $T(I_k)$ and $T(I_{k'})$, that is, an elapsed time, between an abnormal image $I_k$ to be processed (k is a natural number) and an adjacent abnormal image $I_{k'}$ (k' is a natural number, where k<k') in an abnormal image sequence.

In the following step S502, the abnormal image group extracting unit 510 determines whether the abnormal region in the abnormal image $I_k$ is classified as being continuous (see step S54).

When the abnormal region is classified as being continuous (step S502: Yes), the abnormal image group extracting unit 510 determines whether the difference $\Delta T$ between imaging time is not more than a predetermined threshold th5 (step S503).

When the difference $\Delta T$ between imaging time is not more than the threshold th5 (step S503: Yes), the abnormal image group extracting unit 510 then determines whether the global similarity $s_{global}$ between the abnormal images $I_k$ and $I_{k'}$ is not less than a predetermined threshold th6 (step S504).

When the global similarity $s_{global}$ is not less than the threshold th6 (step S504: Yes), the abnormal image group extracting unit 510 determines that the abnormal image $I_k$ to be processed and the abnormal image $I_{k'}$ extracted subsequent to the abnormal image $I_k$ include identical abnormal regions (step S505).

In contrast, when the difference ΔT between imaging time is larger than the threshold th5 in step S503 (step S503: No), or when the global similarity $s_{global}$ is less than the threshold th6 in step S504 (step S504: No), the abnormal image group extracting unit 510 determines that the abnormal image $I_k$ to be processed and the abnormal image $I_{k'}$ extracted subsequent to the abnormal image $I_k$ do not include identical abnormal regions (step S506).

In step S502, when the abnormal region is not classified as being continuous (step S502: No), the abnormal image group extracting unit 510 then determines whether the abnormal region is classified as being intermittent (step S507).

If the abnormal region is classified as being intermittent (step S507: Yes), the abnormal image group extracting unit 510 determines whether the difference ΔT between imaging time is not more than a predetermined threshold th7 (step S508). Here, if the abnormal region is classified as being intermittently-occurring abnormal region, identical abnormal regions may be intermittently shown in a series of time-series images. Therefore, the threshold th7 is set to be longer than the threshold th5 used in step S503.

When the difference ΔT between imaging time is not more than the threshold th7 (step S508: Yes), the abnormal image group extracting unit 510 then determines whether the local similarity $s_{local}$ between the abnormal images $I_k$ and $I_{k'}$ is not less than a predetermined threshold th8 (step S509).

When the local similarity $s_{local}$ is not less than the threshold th8 (step S509: Yes), the abnormal image group extracting unit 510 determines that the abnormal image $I_k$ to be processed and the abnormal image $I_{k'}$ extracted subsequent to the abnormal image Ik include identical abnormal regions (step S505).

In contrast, when the difference ΔT between imaging time is larger than the threshold th7 in step S508 (step S508: No), or when the local similarity $s_{local}$ is less than the threshold th8 in step S509 (step S509: No), the abnormal image group extracting unit 510 determines that the abnormal image $I_k$ to be processed and the abnormal image $I_{k'}$ extracted subsequent to the abnormal image $I_k$ do not include identical abnormal regions (step S506).

When the abnormal region is not classified as being intermittent in step S507 (step S507: No), the abnormal image group extracting unit 510 determines whether the difference ΔT between imaging time is not more than a predetermined threshold th9 (step S510). Here, if the abnormal region is not a continuously-occurring abnormal regions or intermittently-occurring abnormal regions, the threshold th9 is set to a value between the threshold th5 used in step S503 and the threshold th7 used in step S508.

When the difference ΔT between imaging time is not more than the threshold th9 (step S510: Yes), the abnormal image group extracting unit 510 then determines whether the global similarity $s_{global}$ between the abnormal images $I_k$ and $I_{k'}$ is not less than the predetermined threshold th6, and the local similarity $s_{local}$ therebetween is not less than the predetermined threshold th8 (step S511).

When the global similarity $s_{global}$ is not less than the threshold th6 and the local similarity $s_{local}$ is not less than the predetermined threshold th8 (step S511: Yes), the abnormal image group extracting unit 510 determines that the abnormal image $I_k$ to be processed and the abnormal image $I_{k'}$ extracted subsequent to the abnormal image $I_k$ include identical abnormal regions (step S505).

In contrast, when the difference ΔT between imaging time is larger than the threshold th9 in step S510 (step S510: No), or when the global similarity $s_{global}$ is less than the threshold th6 or the local similarity $s_{local}$ is less than the threshold th8, in step S511 (step S511: No), the abnormal image group extracting unit 510 determines that the abnormal image $I_k$ to be processed and the abnormal image $I_{k'}$ extracted subsequent to the abnormal image $I_k$ do not include identical abnormal regions (step S506).

After completion of the processing of the loop E for all abnormal images, the abnormal image group extracting unit 510 extracts abnormal images determined to show the identical abnormal regions, as the identical abnormal image group, in step S512. Then, operation of the image processing apparatus returns to a main routine.

Steps S14 and S15 subsequent to step S55 are similar to those of the first embodiment (see FIG. 2).

As described above, according to the fifth embodiment of the present invention, the threshold used for determining the difference ΔT between imaging time is changed, and the similarities (global similarity $s_{global}$, local similarity $s_{local}$) used for determining a similarity between the abnormal images are switched, according to the types of the subject in the abnormal region, and thus, accuracy in extraction of an abnormal image group including identical abnormal regions can be increased.

Note that, in the fifth embodiment, the determination criteria, which are respectively used for determining the abnormal region by the continuous abnormality determination unit 311 and the intermittent abnormality determination unit 331 may be adjusted to classify all abnormal regions into any of the abnormal regions occurring continuously and the abnormal regions occurring intermittently. In this configuration, steps S510 and S511 described above are omitted.

Modification 5-1

Next, modification 5-1 of the fifth embodiment of the present invention will be described.

In the calculation unit 500 illustrated in FIG. 21, instead of the abnormality classifying unit 340, the abnormality classifying unit 310 only including the continuous abnormality determination unit 311 illustrated in FIG. 13 may be provided to classify the abnormal regions to be processed, into two abnormal regions, that is, the abnormal regions occurring continuously and the other abnormal regions (see third embodiment). In this configuration, in step S502 illustrated in FIG. 23, if the abnormal regions to be processed do not continuously occur (step S502: No), the abnormal regions to be processed are regarded as the abnormal regions occurring intermittently, and the process directly proceeds to step S508. In addition, in this configuration, step S510 and S511 are omitted.

Modification 5-2

Next, modification 5-2 of the fifth embodiment of the present invention will be described.

In the calculation unit 500 illustrated in FIG. 21, instead of the abnormality classifying unit 340, the abnormality classifying unit 330 only including the intermittent abnormality determination unit 331 illustrated in FIG. 16 may be provided to classify the abnormal regions to be processed, into two abnormal regions, that is, the abnormal regions occurring intermittently and the other abnormal regions (see Modification 3-1). In this configuration, after step S501 illustrated in FIG. 23, the process directly proceeds to step S507. Then, in step S507, if the abnormal regions to be processed do not intermittently occur (step S507: No), the abnormal regions to be processed are regarded as the abnormal regions occurring continuously, and the process proceeds to step S503. In addition, in this configuration, step S510 and S511 are omitted.

Modification 5-3

Next, modification 5-3 of the fifth embodiment of the present invention will be described.

In step S55 illustrated in FIG. 22, the abnormal image group extracting unit 510 may extract an abnormal image group including identical abnormal regions, based on the total determination parameter using the positional information, the global similarity, and the local similarity.

Figure 24:
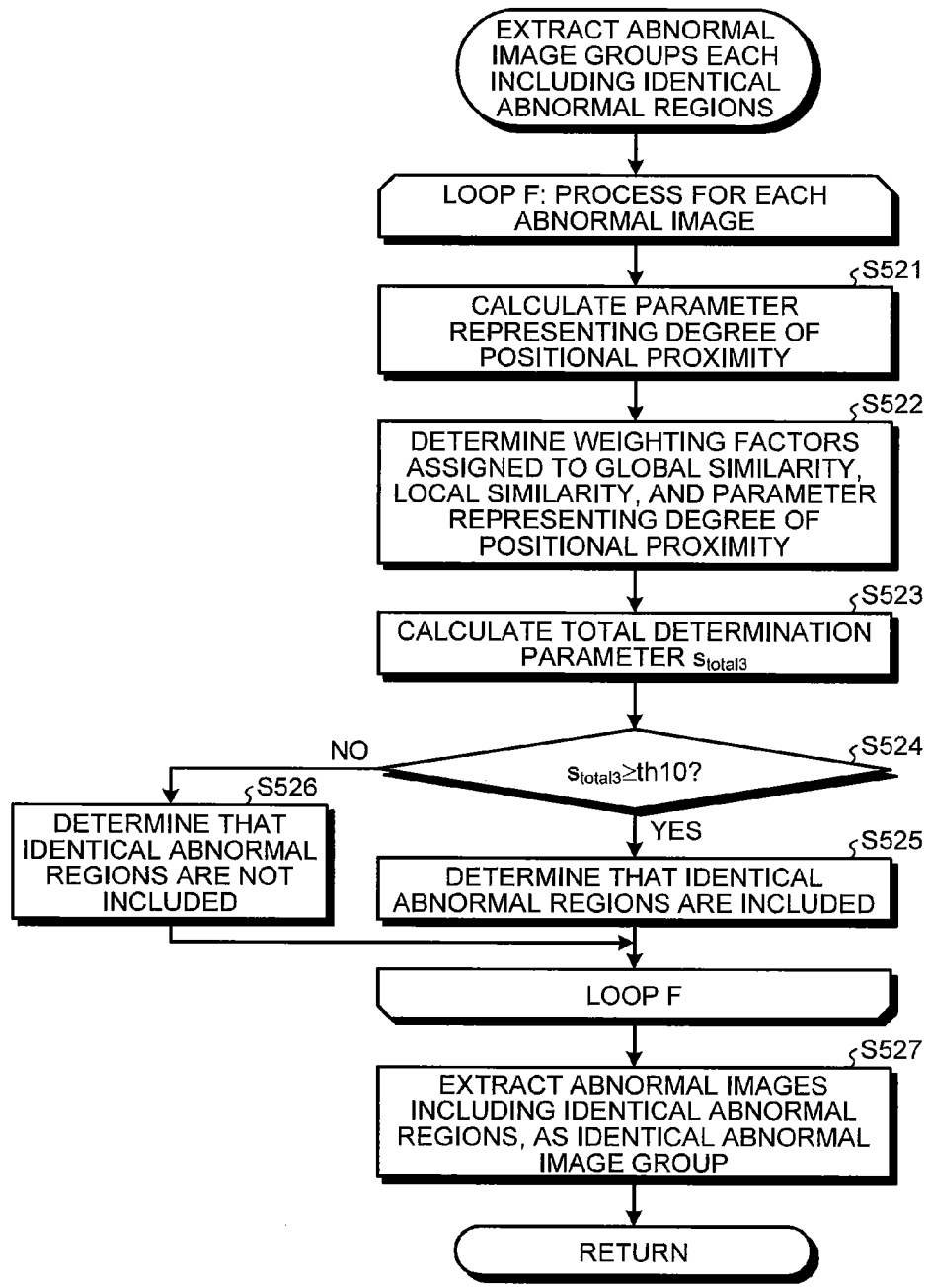
FIG. 24 is a flowchart illustrating an abnormal image group extraction process according to modification 5-3 of the fifth embodiment of the present invention.

FIG. 24 is a flowchart illustrating an abnormal image group extraction process performed by the abnormal image group extracting unit 510 according to modification 5-3. The abnormal image group extracting unit 510 performs processing of a loop F for each abnormal image extracted in step S11.

First, in step S521, the abnormal image group extracting unit 510 calculates a parameter $s_{pos}$ ($s_{pos}$=(N−n)/N) representing a degree of positional proximity between an abnormal image $I_j$ (j is a natural number) to be processed, and an abnormal image $I_{j+n}$ (n is a natural number) adjacent to the abnormal image $I_j$ in an abnormal image sequence. Note that, in step S51, when imaging time of the abnormal images $I_i$ is acquired as the positional information, a parameter representing a degree of positional proximity may be calculated based on a difference between imaging time.

In the following step S522, the abnormal image group extracting unit 510 determines weighting factors $w_5$, $w_6$, and $w_7$ ($w_5+w_6+w_7=1$) assigned to the global similarity $s_{global}$, the local similarity $s_{local}$, and the parameter $s_{pos}$ representing the degree of positional proximity, respectively, based on a result of the classification of the abnormal regions in the abnormal images to be processed (see step S54).

The weighting factors $w_5$, $w_6$, and $w_7$ are set so that if the abnormal image $I_j$ has an abnormal region occurring continuously, the weighting factor $w_7$ is relatively larger, and the weighting factor $w_5$ is relatively larger between the weighting factors $w_5$ and $w_6$. In contrast, if the abnormal region occurs intermittently, the weighting factor $w_7$ is relatively smaller, and the weighting factor $w_6$ is relatively larger between the weighting factors $w_5$ and $w_6$.

In the following step S523, the abnormal image group extracting unit 510 uses the weighting factors $w_5$, $w_6$, and $w_7$ determined in step S522 to calculate a total determination parameter $s_{total3}$ to which the global similarity $s_{global}$, the local similarity $s_{local}$, and the parameter $s_{pos}$ representing the degree of positional proximity are added. The total determination parameter $s_{total3}$ is given by the following formula (6).

$$s_{total3}=w_5 \cdot s_{global}+w_6 \cdot s_{local}+w_7 \cdot s_{pos} \quad (6)$$

In the following step S524, the abnormal image group extracting unit 510 determines whether the total determination parameter $s_{total3}$ is not less than a predetermined threshold th10. When the total determination parameter $s_{total3}$ is not less than the threshold th10 (step S524: Yes), the abnormal image group extracting unit 510 determines that the abnormal image to be processed and the abnormal image extracted subsequent to the abnormal image include identical abnormal regions (step S525). In contrast, when the total determination parameter $s_{total3}$ is less than the threshold th10 (step S524: No), the abnormal image group extracting unit 510 determines that the abnormal image $I_j$ to be processed and the abnormal image $I_{j+n}$ extracted subsequent to the abnormal image do not include identical abnormal regions (step S526).

After completion of the processing of the loop F for all abnormal images, the abnormal image group extracting unit 510 extracts abnormal images determined to show identical abnormal regions, as the identical abnormal image group, in step S527. Then, operation of the image processing apparatus returns to a main routine.

In the first to fifth embodiments and the modifications thereof having been described above, different abnormal images having a global similarity or a determination parameter calculated based on the global similarity, not less than a predetermined threshold are determined to include identical abnormal regions, but the abnormal images having a global similarity or a determination parameter not more than the predetermined threshold may be determined to include identical abnormal regions, depending on a method of calculating the global similarity or the determination parameter.

The image processing apparatus according to the first to fifth embodiments and modifications thereof described above can be achieved by executing image processing programs recorded in a recording medium, on a computer system such as a personal computer or workstation. Furthermore, such a computer system may be used by being connected to another computer system or a device such as a server, through a local area network (LAN), a wide area network (WAN), or a public network such as the Internet. In this configuration, the image processing apparatus according to the first to fifth embodiments and modifications thereof may acquire image data of the intraluminal images through these networks, output a result of image processing to various output devices (viewer, printer, and the like) connected through these networks, or store a result of image processing in a storage device (recording medium, reader thereof, and the like) connected through these networks.

According to some embodiments, since an image-of-interest group is extracted from images of interest detected from a group of a series of images, based on a global similarity between the images of interest, it is possible to prevent abnormal images showing identical abnormal regions from being continuously extracted as representative images.

Note that, the present invention is not limited to the first to fifth embodiments and modifications thereof, and invention can be variously made by appropriately combining the elements disclosed in the embodiments or modifications. For example, the present invention may be made by excluding several elements from all the elements described in the embodiments or modifications, or by appropriately combining the elements described in different embodiments or modifications.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a detecting unit configured to detect images of interest including regions of interest that are estimated as an object to be detected, from a group of a series of images acquired by sequentially imaging a lumen of a living body;

a global similarity calculating unit configured to calculate a global similarity that is a similarity between regions including at least regions other than the regions of interest, between the images of interest different from one another;

an image-of-interest group extracting unit configured to extract an image-of-interest group including identical regions of interest, in accordance with comparison between a threshold and the global similarity or a determination parameter based on the global similarity; and a representative image extracting unit configured to extract a representative image from the image-of-interest group.

2. The image processing apparatus according to claim 1, wherein
the global similarity calculating unit is configured to extract background regions from the images of interest, and to calculate the similarity between the background regions, between the images of interest different from one another.

3. The image processing apparatus according to claim 2, wherein
the global similarity calculating unit is configured to extract, as the background regions, regions excluding the regions of interest from the images of interest.

4. The image processing apparatus according to claim 2, wherein
the global similarity calculating unit is configured to extract, as the background regions, regions showing a mucosa from the images of interest.

5. The image processing apparatus according to claim 1, further comprising a local similarity calculating unit configured to calculate a local similarity that is a similarity between the regions of interest, between the images of interest different from one another, wherein
the image-of-interest group extracting unit is configured to extract the image-of-interest group including the identical regions of interest, based on the global similarity and the local similarity.

6. The image processing apparatus according to claim 5, wherein
the local similarity calculating unit is configured to match the regions of interest with one another, and to calculate the local similarity based on a result of matching the regions of interest with one another.

7. The image processing apparatus according to claim 5, further comprising a region-of-interest classifying unit configured to classify the regions of interest according to types of a subject in the regions of interest, wherein
the determination parameter is given by weighting and adding the global similarity and the local similarity, and
the image-of-interest group extracting unit is configured to change weighting factors assigned to the global similarity and the local similarity, according to a result of classification by the region-of-interest classifying unit, thereby to extract the image-of-interest group.

8. The image processing apparatus according to claim 7, wherein
the image-of-interest group extracting unit is configured to extract images of interest having the determination parameter not less than the threshold, as the image-of-interest group including the identical regions of interest.

9. The image processing apparatus according to claim 7, wherein
the region-of-interest classifying unit comprises an intermittency determination unit configured to determine whether the regions of interest occur intermittently in the group of a series of images, and
if the regions of interest occur intermittently, the image-of-interest group extracting unit is configured to set a weighting factor for the local similarity to be larger than a weighting factor for the global similarity.

10. The image processing apparatus according to claim 9, wherein
if a subject in the regions of interest is one of redness, bleeding point, and ulcer, the intermittency determination unit is configured to determine that the regions of interest occur intermittently.

11. The image processing apparatus according to claim 7, wherein
the region-of-interest classifying unit comprises a continuity determination unit configured to determine whether the regions of interest occur continuously in the group of a series of images, and
if the regions of interest occur continuously, the image-of-interest group extracting unit is configured to set a weighting factor for the global similarity to be larger than a weighting factor for the local similarity.

12. The image processing apparatus according to claim 11, wherein
if a subject in the regions of interest is one of floating blood and vascular abnormality, the continuity determination unit is configured to determine that the regions of interest occur continuously.

13. The image processing apparatus according to claim 1, further comprising a positional information acquiring unit configured to acquire time-series positional information corresponding to order of capturing the images of interest in the group of a series of images, wherein
the image-of-interest group extracting unit is configured to extract the image-of-interest group including the identical regions of interest, based on the global similarity and the positional information.

14. The image processing apparatus according to claim 13, further comprising a region-of-interest classifying unit configured to classify the regions of interest, wherein
the determination parameter is given by weighting and adding the global similarity and a parameter representing a degree of proximity between the images of interest different from one another based on the positional information,
the image-of-interest group extracting unit is configured to change weighting factors assigned to the global similarity and the parameter representing the degree of proximity, according to a result of classification by the region-of-interest classifying unit, thereby to extract the image-of-interest group.

15. The image processing apparatus according to claim 14, wherein
the parameter representing the degree of proximity has a larger value as the images of interest different from one another are provided more closely to one another, and
the image-of-interest group extracting unit is configured to extract images of interest having the determination parameter not less than the threshold, as the image-of-interest group including the identical regions of interest.

16. The image processing apparatus according to claim 14, wherein the region-of-interest classifying unit comprises an intermittency determination unit configured to determine whether the regions of interest occur intermittently in the group of a series of images, and if the regions of interest occur intermittently, the image-of-interest group extracting unit is configured to set a weighting factor for the global similarity to be larger than a weighting factor for the parameter representing the degree of proximity.

17. The image processing apparatus according to claim 16, wherein if a subject in the regions of interest is one of redness, bleeding point, and ulcer, the intermittency determination unit is configured to determine that the regions of interest occur intermittently.

18. The image processing apparatus according to claim 14, wherein the region-of-interest classifying unit comprises a continuity determination unit configured to determine whether the regions of interest occur continuously in the group of a series of images, and if the regions of interest occur continuously, the image-of-interest group extracting unit is configured to set a weighting factor for the parameter representing the degree of proximity to be larger than a weighting factor for the global similarity.

19. The image processing apparatus according to claim 18, wherein if a subject in the regions of interest is one of floating blood and vascular abnormality, the continuity determination unit is configured to determine that the regions of interest occur continuously.

20. The image processing apparatus according to claim 1, wherein the image-of-interest group extracting unit is configured to extract images of interest having the global similarity not less than the threshold, as the image-of-interest group including the identical regions of interest.

21. An image processing method for causing a calculation unit of a computer to perform image processing based on image data of a group of a series of images which are acquired by sequentially imaging a lumen of a living body and recorded in a recording unit, the method comprising:

detecting images of interest including regions of interest, from the group of a series of images;

calculating a global similarity that is a similarity between regions including at least regions other than the regions of interest, between the images of interest different from one another;

extracting an image-of-interest group including identical regions of interest, in accordance with comparison between a threshold and the global similarity or a determination parameter based on the global similarity; and extracting a representative image from the image-of-interest group.

22. A non-transitory computer-readable recording medium with an executable program stored thereon, the program causing a computer to execute:

detecting images of interest including regions of interest, from a group of a series of images acquired by sequentially imaging a lumen of a living body;

calculating a global similarity that is a similarity between regions including at least regions other than the regions of interest, between the images of interest different from one another;

extracting an image-of-interest group including identical regions of interest, in accordance with comparison between a threshold and the global similarity or a determination parameter based on the global similarity; and extracting a representative image from the image-of-interest group.

* * * * *